(12) United States Patent
Gupta

(10) Patent No.: US 11,821,866 B2
(45) Date of Patent: *Nov. 21, 2023

(54) NANOSCALE ELECTROCHEMICAL INTERFACE FOR DETECTION OF ANALYTES

(71) Applicants: ProbiusDx, Inc., El Cerrito, CA (US); The Board of Trustees of the Leland Stanford Junior University, Palo Alto, CA (US)

(72) Inventor: Chaitanya Gupta, San Carlos, CA (US)

(73) Assignees: ProbiusDx, Inc., El Cerrito, CA (US); The Board of Trustees of the Leland Stanford Junior University, Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/688,329

(22) Filed: Mar. 7, 2022

(65) Prior Publication Data
US 2022/0299462 A1 Sep. 22, 2022

Related U.S. Application Data

(63) Continuation of application No. 16/016,468, filed on Jun. 22, 2018, now Pat. No. 11,268,924.

(Continued)

(51) Int. Cl.
*G01N 27/30* (2006.01)
*G01N 27/48* (2006.01)
(Continued)

(52) U.S. Cl.
CPC ........... *G01N 27/30* (2013.01); *G01N 27/416* (2013.01); *G01N 27/48* (2013.01); *B82Y 15/00* (2013.01)

(58) Field of Classification Search
CPC ............ G01N 27/327; G01N 27/4145; G01N 27/4148; G01N 27/30; G01N 27/48
See application file for complete search history.

(56) References Cited

U.S. PATENT DOCUMENTS

| | | |
|---|---|---|
| 5,198,771 A | 3/1993 | Fidler et al. |
| 5,389,224 A | 2/1995 | Hetrick |

(Continued)

FOREIGN PATENT DOCUMENTS

| | | |
|---|---|---|
| CN | 105229452 A | 1/2016 |
| EP | 2 437 048 A1 | 4/2012 |

(Continued)

OTHER PUBLICATIONS

Anderson, et al., "Single-Nanoparticle Electrochemistry Through Immobilization and Collision". Acc. Chem. Res. 2016, 49 (11), 2625-2631.

(Continued)

*Primary Examiner* — Caitlyn Mingyun Sun
(74) *Attorney, Agent, or Firm* — Mintz Levin Cohn Ferris Glovsky and Popeo, P.C.

(57) ABSTRACT

A sensor can selectively detect quantum signatures in charge transfer processes via a tunneling current. In one aspect, the sensor can include a metal electrode having a first surface and a second surface. The sensor can also include an insulator film having a first thickness, a first surface area and a first surface chemistry. The insulator film can be coupled to the metal electrode via the first surface. The sensor can also include a functionalization film having a second thickness, a second surface area and a second surface chemistry. The functionalization film can be coupled to the metal electrode via the second surface. The insulator film and the (Continued)

functionalization film are configured to separate the metal electrode from an electrochemical solution comprising the analyte.

20 Claims, 17 Drawing Sheets

Related U.S. Application Data

(60) Provisional application No. 62/523,729, filed on Jun. 22, 2017.

(51) Int. Cl.
*G01N 27/416* (2006.01)
*B82Y 15/00* (2011.01)

(56) References Cited

U.S. PATENT DOCUMENTS

| | | | |
|---|---|---|---|
| 7,785,785 B2 * | 8/2010 | Pourmand | G01N 27/3275 422/68.1 |
| 8,901,620 B2 | 12/2014 | Lee et al. | |
| 8,951,400 B2 * | 2/2015 | Ahrens | C07F 15/002 205/67 |
| 9,285,336 B2 * | 3/2016 | Gupta | B82Y 15/00 |
| 11,268,924 B2 | 3/2022 | Gupta | |
| 2010/0149544 A1 | 6/2010 | Ghislain | |
| 2010/0270174 A1 | 10/2010 | Chen et al. | |
| 2011/0114511 A1 | 5/2011 | Sjong | |
| 2015/0041337 A1 | 2/2015 | Gupta | |
| 2017/0008825 A1 * | 1/2017 | Johnson | C07C 37/07 |

FOREIGN PATENT DOCUMENTS

| | | |
|---|---|---|
| GB | 1 505 343 A | 3/1978 |
| WO | WO-2008/045799 A2 | 4/2008 |
| WO | WO-2008/045799 A3 | 4/2008 |
| WO | WO-2010/120364 A2 | 10/2010 |
| WO | WO-2014/146171 A1 | 9/2014 |
| WO | WO-2018/237348 A1 | 12/2018 |

OTHER PUBLICATIONS

Extended European Search Report dated Mar. 5, 2021, for EP Patent Application No. 18820747.6, 8 pages.

Gooding, et al., "Nanoparticle Mediated Electron Transfer Across Organic Layers: From Current Understanding to Applications". J. Braz. Chem. Soc., 2014, 25(3), 418-426.

Gupta, C. (2012). "Electrochemical quantum tunneling for electronic detection and characterization of biological toxins," Proc. SPIE 8373, Micro- and Nanotechnology Sensors, Systems, and Application IV, 837303, 2012, p. 1-14.

Gupta, C. et al. (Dec. 15, 2016). "Active Control of Probability Amplitudes in a Mesoscale System via Feedback-Induced Suppression of Dissipation and Noise," Journal of Applied Physics 120, 224902.

International Search Report and Written Opinion issued in corresponding International Application No._PCT/ US18/39140, dated Sep. 19, 2018, 34 pages.

International Preliminary Report on Patentablility issued in corresponding International Application No. PCT/ US18/39140, dated Dec. 24, 2019, 8 pages.

* cited by examiner

5nm NP, 50nm pore, ruthenium hexaamine couple

5nm NP, 1000nm pore, ferro-/ferricyanide couple

| | |
|---|---|
| Characteristic frequency $\Omega_\infty$ (Energy = 0.1eV) | $1.52 \times 10^{14}$/s |
| $c_s A_s$ ($A_s \sim (50\text{nm})^2$) | $1.314 \times 10^{-16}$ F |
| $c_r A_s$ | $1.314 \times 10^{-16}$ F |
| $c_{geom} A_s$ ($\delta \sim 5 \times 10^{-10}$ m) | $8.85 \times 10^{-17}$ F |
| $c_{par} A_{par}$ ($A_{par} \sim (2\mu\text{m})^2$) | $8 \times 10^{-15}$ F |
| $C_{tot}$ Estimated from measurement of hysteresis | $3.7 \times 10^{-16}$ F |

Table 1: Values of relevant interfacial capacitance components, as estimated from dimensions of the experimental system and estimation of total equivalent interfacial capacitance from measured hysteresis in I-V trace.

FIG. 12

NANOSCALE ELECTROCHEMICAL INTERFACE FOR DETECTION OF ANALYTES

CROSS-REFERENCE TO RELATED APPLICATION

This application is a continuation of U.S. patent application Ser. No. 16/016,468, filed Jun. 22, 2018, which claims priority to U.S. Provisional Patent Application No. 62/523,729, filed Jun. 22, 2017, titled "NANOSCALE ELECTROCHEMICAL INTERFACE FOR DETECTION OF ANALYTES," hereby incorporated by reference in their entireties.

STATEMENT REGARDING FEDERALLY SPONSORED RESEARCH OR DEVELOPMENT

This invention was made with government support under grant N66001-11-1-4111 awarded by Defense and Advanced Research Projects Agency. The government has certain rights in the invention.

TECHNICAL FIELD

The subject matter described herein relates to detection of analytes.

BACKGROUND

A potentiostat is commonly used in electrochemical experiments to probe properties of a physical system, for example, an electrochemical interface between a solid and liquid phase. A potentiostat employs a three electrode system comprising a reference electrode, a working electrode and a counter electrode. The potentiostat can operate by maintaining a fixed potential difference between a working electrode and a reference electrode and measuring the current that flows through the electrolyte and across the working electrode-electrolyte interface via the counter electrode. For example, in bulk electrolysis experiments, a potentiostat can be used to measure the total charge that has transferred across an electrochemical interface at a fixed potential difference. The measured charge can be indicative of the reduction/oxidation reaction at the interface.

The physical system (e.g., electrode-electrolyte interface) probed by the potentiostat can include one or more systems that exhibit quantum properties, e.g., transport properties associated with mesoscale phenomena (phenomena that lie in between the classical and quantum-mechanical regimes of behavior). Traditional potentiostats are limited in their ability to detect quantum properties at room temperature in electrochemical systems. Additionally, traditional potentiostats are unable to selectively detect quantum signatures of the physical system. For example, traditional potentiostats have not been designed to selectively detect a predetermined range of values of a quantum property that can be indicative of a phenomenon or a target (e.g., a target analyte) under detection. Selective detection of quantum properties can be important for novel sensing, timing and communication paradigms. Therefore, it is desirable to develop a potentiostat that can selectively detect a quantum property of a physical system (e.g., electrode-electrolyte interface).

SUMMARY

This application provides for a nanoscale electrochemical interface (also referred to as "a sensor") that allows for selective detection of quantum signatures in a charge transfer processes at the electrochemical interface. For example, a tunneling current resulting from charge transfer processes at the electrochemical interface can interact with polarization modes of various analytes at the interface. These interactions can result in modulations in the tunneling current. The nanoscale electrochemical interface can be designed to preferentially detect certain modulations in the tunneling current that can be indicative of a polarization mode or a range of polarization modes of a predetermined analyte at the interface. Designing a nanoscale electrochemical interface for preferential detection of predetermined modulations in the tunneling current can improve the accuracy and efficiency of analyte detection. For example, a nanoscale electrochemical interface configured to selectively detect a polarization mode (or a range of polarization modes) of a predetermined analyte is less likely to erroneously detect polarization modes associated with a different analyte at the electrochemical interface. This can improve the accuracy of analyte detection. Selective detection of an analyte polarization mode can improve the accuracy and efficiency of analytics routine used to determine polarization current information from the detected tunneling current. For example, if a nanoscale interface is configured to selectively detect a predetermined polarization mode, the analytics routine can be programmed to look for information associated with the predetermined polarization mode in the tunneling current. This can improve the analytics processing time, and as a result, provide for quick detection of analytes.

Accordingly, in one aspect, a sensor configured to detect one or more analytes is provided. The sensor includes at least: (a) a metal electrode having a first surface and a second surface; (b) an insulator film having a first thickness, a first surface area and a first surface chemistry, the insulator film coupled to the metal electrode via the first surface; and (c) a functionalization film having a second thickness, a second surface area and a second surface chemistry, the functionalization film coupled to the metal electrode via the second surface. The insulator film and the functionalization film are configured to separate the metal electrode from an electrochemical solution comprising the analyte. In another aspect, the sensor includes a nanoparticle coupled to the metal electrode via a molecular linker. In another aspect, a thickness of the molecular linker is less than the second thickness of the functionalization film.

In any of the aspects above and herein, the insulator film has a first dielectric constant and the functionalization film has a second dielectric constant different from the first dielectric constant. In any of the aspects above and herein, one or more of the first surface area, the first thickness, the first dielectric constant and the first surface chemistry are determined based on a threshold characteristic capacitance associated with the metal electrode and the electrochemical solution. In any of the aspects above and herein, one or more of the second surface area, the second thickness, the second dielectric constant and the second surface chemistry are determined based on a characteristic charge distribution at an interface between the sensor and the electrochemical solution, wherein the interface is configured to transfer current between the sensor and the electrochemical solution, the transferred current indicative of the analyte. In any of the aspects above and herein, the electrochemical solution comprises one or more redox active species. In any of the aspects above and herein, the one or more redox species are determined based on characteristic reorganization energies of the one or more redox species. In any of the aspects above and herein, a transfer of charge occurs between the redox active species and the metal electrode via a portion of the functionalization film, wherein the metal electrode is biased relative to the electrochemical solution. In any of the aspects above and herein, the insulator film includes a shielding mechanism configured to shield the metal electrode from a parasitic capacitance associated with the electrochemical solution. In any of the aspects above and herein, the second surface area is determined based on a characteristic frequency of one or more polarization modes of a redox specie in the electrochemical solution, wherein the redox specie is configured to transfer charge to the metal electrode via the functionalization film.

In one aspect, a system to detect one or more analytes is provided. The system includes at least: (a) a first electrode configured to electrically couple to an electrochemical solution; (b) a second electrode configured to electrically couple to the electrochemical solution; (c) a third electrode including a sensor configured to detect an analyte in the electrochemical solution, the includes at least: (i) a metal electrode having a first surface and a second surface; (ii) an insulator film having a first thickness, a first surface area and a first surface chemistry, the insulator film coupled to the metal electrode via the first surface; and (iii) a functionalization film having a second thickness, a second surface area and a second surface chemistry, the functionalization film coupled to the metal electrode via the second surface, wherein the insulator film and the functionalization film are configured to separate the metal electrode from the electrochemical solution. The system also includes a feedback mechanism coupled to the first, the second and the third electrode, the feedback mechanism configured to provide an excitation control to the electrochemical solution at the third electrode. In another aspect, the sensor further comprises a nanoparticle coupled to the metal electrode via a molecular linker. In another aspect, a thickness of the molecular linker is less than the second thickness of the functionalization film.

In any of the aspects above and herein, the insulator film has a first dielectric constant and the functionalization film has a second dielectric constant different from the first dielectric constant. In any of the aspects above and herein, one or more of the first surface area, the first thickness, the first dielectric constant and the first surface chemistry are determined based on a threshold characteristic capacitance associated with the metal electrode and the electrochemical solution. In any of the aspects above and herein, one or more of the second surface area, the second thickness, the second dielectric constant and the second surface chemistry are determined based on a characteristic charge distribution at an interface between the sensor and the electrochemical solution, wherein the interface is configured to transfer current between the sensor and the electrochemical solution, the transferred current indicative of the analyte. In any of the aspects above and herein, the electrochemical solution comprises one or more redox active species. In any of the aspects above and herein, the one or more redox species are determined based on characteristic reorganization energies of the one or more redox species. In any of the aspects above and herein, a transfer of charge occurs between the redox active species and the metal electrode via a portion of the functionalization film, wherein the metal electrode is biased relative to the electrochemical solution. In any of the aspects above and herein, the insulator film includes a shielding mechanism configured to shield the metal electrode from a parasitic capacitance associated with the electrochemical solution. In any of the aspects above and herein, the second surface area is determined based on a characteristic frequency of one or more polarization modes of a redox specie in the electrochemical solution, wherein the redox specie is configured to transfer charge to the metal electrode via the functionalization film.

In any of the aspects above and herein, the feedback mechanism is configured to detect a potential associated with the electrochemical solution via the first electrode, and provide a feedback signal to the electrochemical solution via the second electrode. In any of the aspects above and herein, the first, second and third electrodes are a reference electrode, a counter electrode and a working electrode of a potentiostat, respectively. In any of the aspects above and herein, the feedback mechanism comprises a first negative-feedback amplifier configured to generate a first signal based on a difference between the detected potential and a set potential value. In any of the aspects above and herein, the feedback mechanism comprises a second negative feedback amplifier configured to receive the first signal and generate the feedback signal. In any of the aspects above and herein, the excitation control reduces dissipative coupling of one or more vibronic energy levels in a redox specie in the electrochemical solution to an external bath. In any of the aspects above and herein, the system includes a current detection system configured to detect a current associated with the second electrode. In any of the aspects above and herein, the detected current is indicative of an analyte in the molecular-scale charge transfer system.

In one aspect, a method to detect one or more analytes is provided. The method includes at least: (a) detecting, by a feedback mechanism via a first electrode of a plurality of electrodes, a potential associated with an electrochemical solution, wherein the plurality of electrodes electrically coupled to the electrochemical solution; (b) generating, by the feedback mechanism, a feedback signal; and (c) providing the feedback signal to the electrochemical solution via a second electrode of the plurality of electrodes, the feedback signal configured to provide excitation control of the sample at a third electrode of the plurality of electrode, wherein the third electrode includes a sensor configured to detect the analyte in the electrochemical solution, the sensor includes at least: (i) a metal electrode having a first surface and a second surface; (ii) an insulator film having a first thickness, a first surface area and a first surface chemistry, the insulator film coupled to the metal electrode via the first surface; and (iii) a functionalization film having a second thickness, a second surface area and a second surface chemistry, the functionalization film coupled to the metal electrode via the second surface, wherein the insulator film and the functionalization film are configured to separate the metal electrode from the electrochemical solution.

DESCRIPTION OF DRAWINGS

FIG. 12 illustrates a table of exemplary values of various components of total interfacial capacitance based on Equations 3.1-3.3.

DETAILED DESCRIPTION

Figure 1:
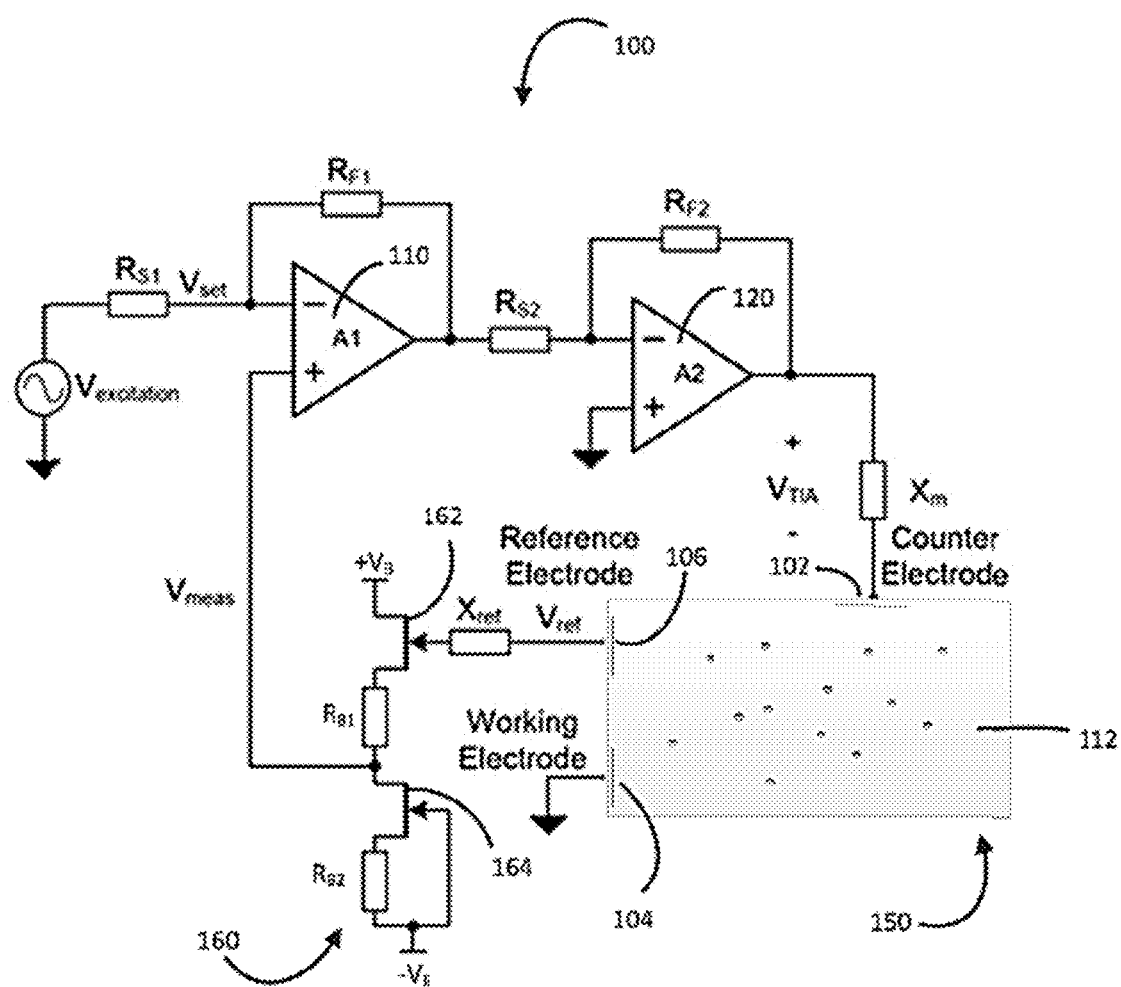
FIG. 1 illustrates an implementation of a potentiostat with a high-gain and low-noise feedback control system.

A nanoscale electrochemical interface ("interface") can be designed to detect analytes present in an electrochemical solution. The interface can be integrated with a potentiostat which can measure electrical properties of the electrochemical solution (e.g., potential of the electrochemical solution, current flowing through the electrochemical solution, etc.) via various metallic or semi-metallic electrodes. For example, the interface can be integrated with the working electrode of the potentiostat where an exchange of electrons between the electrochemical solution and the interface can take place. The electron exchange can result in a tunneling current through the interface which can include quantum signatures of various components/phenomena of the electrochemical solution adjacent to the interface. For example, the tunneling current can include information related to polarization modes of various analytes in the electrochemical solution.

The tunneling current can be detected by a detection system in the potentiostat, and analyzed by an analytics routine to decipher the quantum signatures. Analysis of detected tunneling current can require a complex, multi-scale spatial and temporal physical model for the charge transfer process and the accompanying surface interactions between multiple potential analytes and the interface. An alternative methodology for analysis of the signals generated by these interfaces can utilize reference datasets of signatures from 'pure' analytes for pattern matching and feature identification, as is usually done in spectroscopy-like applications.

Information encoded in the tunneling current can be challenging to decipher. For example, the electron transfer mechanism that generates the tunneling current can determine the information that can be extracted from the tunneling current. The electron transfer process, for example, can be adiabatic or non-adiabatic in nature. The electron transfer process can be affected by interplay of various factors (e.g., dynamics of electrons transitioning from redox species in electrochemical solution to the interface, polarization modes of analytes in the electrochemical solution, polarization environment dielectric environment, and the like). The interface can be designed to act like a filter that suppresses undesired effects of the electrochemical solution on the tunneling current that can impede the accuracy and/or efficiency of analyte detection. The undesired effects can include, for example, noise from dielectrics in the vicinity of charge transfer process (that results in tunneling current), effect from polarization modes of undesired analytes, and the like.

This application provides for techniques for designing an interface to detect a predetermined analyte. The design consideration can be based on, for example, lateral dimension of the interface perpendicular to the charge transfer flux, the thickness and chemistry of a functionalization film on the interface, thickness and dielectric permittivity of insulator on electrode lead utilized for addressing interface node, area of electrode lead, redox chemistry in electrolyte phase, voltage noise at the interface, gain in potentiostatic feedback loop for instrumentation utilized to bias the interface, and the like. These criteria can be represented by macroscopic lumped impedance elements that characterize the equivalent circuit model for the interface. This application describes that the model can reduce to the well-known Randles equivalent circuit in the classical limit. This application also describes the perturbation introduced by traditional electrochemical measurement apparatus on the quantum electrochemical system, and design criteria to minimize these disturbances.

The electrochemical solution can include an electrolyte (e.g., an aqueous solvent, an organic solvent, etc.), a buffering salt, components of a testing sample (e.g., a complex matrix), one or more analyte species, redox species that can serve as charge source or sink to facilitate charge exchange with the electrode, etc. The redox species can include, for example, ferro-/ferricyanide couple, ferrocenium ion and ruthenium hexaamine complex. The analytes can include, for example, whole microorganisms or components thereof including DNA, RNA oligomers, peptide fragments, proteins, glycans, polysaccharides, metabolites etc or other non-biological entities like small molecules.

An interface can be designed based on above-mentioned design considerations to detect analytes in an electrochemical solution. As described before, the interface can be coupled to an electrode (e.g., working electrode) of a potentiostat (also referred to as potentiostatic apparatus). This application describes various embodiments of potentiostats that can include the interface, and can differ, for example, based on feedback circuits, arrangement of electrodes, current/voltage detection systems, etc. This application also describes various electrochemical solutions and analytes (e.g., electrochemical solutions and analytes mentioned above) that can interact with the various embodiments of potentiostats. The various embodiments of potentiostats, and the various electrochemical solutions and analytes do not limit the design or use of the interface.

FIG. 1 illustrates an implementation of a potentiostatic apparatus 100 with a feedback control system coupled to an electrochemical system. The electrochemical system 150 can include molecular-scale charge transfer system (e.g., electrochemical solution 112 and electrode 104), and analytes contained in the electrolyte phase of the system (not shown). The potentiostatic apparatus 100 and the electrochemical system 150 can be electrically coupled via one or more of counter electrode 102, working electrode 104 and reference electrode 106. The potentiostatic apparatus 100 can apply a potential bias across the electrochemical system 150 (e.g., between reference electrode 106 and working electrode 104). The applied bias can result in charge transfer between the redox-active species in electrochemical solution 112 and the nanoscale working electrode 104. The exchange of electrons between the electrodes and the redox species can lead to an exchange of energy, and is referred to as electron energy transfer (EET). The transport of redox species in the electrochemical system 150 can complement the flow of electrons in the potentiostatic apparatus 100 and completes the charge flow circuit.

The current flowing into (or out) of the counter electrode 102 can be related to the exchange of electrons between the redox species and the working electrode 104, for example when the counter electrode is much larger in area than the working electrode and the current flow into the reference electrode 106 is small (e.g., zero). Therefore, measuring the current flowing into (or out) of the counter electrode can be indicative of the rate and nature of electron exchange at the working electrode 104 (or counter electrode 102). The current can be detected, for example, by measuring a voltage difference across an impedance (e.g., $X_m$) electrically coupled to the counter electrode 102. The voltage difference can be measured, for example, by using a low noise voltmeter or transimpedance amplifier chain. In some implementations, the rate of electron exchange at the working electrode 104 can be detected by measuring the current at the working electrode 104 (e.g., by measuring a voltage difference across impedance electrically coupled to the working electrode 104).

Electrons in the redox species can occupy vibration-dressed electronic energy states (also referred to as vibronic states). The electronic exchange between the vibronic states of redox species and the energy states in electrodes can be affected by the environment or thermodynamic bath (e.g., dielectric environment of the solvent). The electronic exchange process can also be affected by the presence of analytes (e.g., analytes present on or near the surface of the working electrodes) and the background matrix of the sample being tested. The interaction between the polarization modes of the analytes (e.g. slow moving vibrational modes of the analyte species) and the vibronic states of redox species can perturb the electronic exchange process. In some cases, the available electronic modes of the analytes can even directly participate in the electron exchange process between the redox species and the working electrode. The effect of the analyte on the electronic exchange process can be detected by measuring the charge exchange current at the interface between the working electrode (104) and the electrochemical solution (112) which can be measured at the counter electrode 102 (or working electrode 104) as described above. By measuring the current for various input voltages Vset, a current versus voltage (I-V) trace for the electrochemical interface 150 (which can include the effect of analyte) can be generated. Analytes in the electrochemical system 150 can be fingerprinted (e.g., their I-V trace determined) by quantifying the perturbation introduced by these analytes on the measured charge transfer flux at the interface.

Thermal disturbances in the electric field energy in proximity to the working electrode 104 can affect the electronic exchange process at the working electrode 104. Thermal disturbances can affect the electronic exchange process between the redox species and the electrodes, and therefore impede the determination of the analyte in the electrochemical system. For example, fluctuations in electric fields can be related proportionally to the dissipation forces acting on the electronic exchange process, which can obfuscate any resonant interactions present in the electrochemical system. The thermal disturbance in the electric field can arise due to the intrinsic electrostatic environment at the electrochemical interface or due to electronic noise injected from the biasing and current-measurement circuitry (e.g., from the reference electrode 106, counter electrode 102 etc.) coupled to the electrochemical system. Thermal disturbances can scale with the temperature of the system making the detection of analytes difficult at ambient conditions (for example, above 50 K).

A feedback control system in the potentiostatic apparatus 100 can mitigate the effect of thermal disturbances and dissipation, and therefore allow for the detection of analytes, for example, via resonant signatures in the electronic exchange process at room temperatures. The feedback control system can apply the desired bias across the electrochemical interface between the electrochemical solution 112 and the working electrode 104 utilizing negative feedback, and can suppress intrinsic and reduce (e.g., minimize) extrinsic sources of thermal disturbance.

As shown in FIG. 1, the feedback control system comprises a pair of ultra-low noise amplifiers 110 and 120 that are electrically coupled to the electrochemical system 150 via the counter electrode 102 and the reference electrode 106. The feedback control system detects the potential Vref of the redox active species in the electrochemical solution 112 at the reference electrode 106. Vref can be representative of the vibronic energy of the redox species in the electrochemical solution 112.

In some implementations, the feedback control system can include a low noise voltage buffer 160 that has high impedance, and can detect the potential Vref with minimal perturbation to the electrochemical solution 112. As shown in FIG. 1, the voltage buffer comprises cascaded field effect transistors 162 and 164 (e.g., pMOS, nMOS transistors). The voltage buffer 160 can generate a voltage signal Vmeas (at the drain of the transistor 164) which represents the voltage Vref detected by the voltage buffer 160 at the reference electrode 106. Pair of cascaded amplifiers 110 and 120 (having a gain of A1 and A2, respectively) are configured to deliver a high gain, low noise corrective signal to the electrochemical system 150 via the counter electrode 102. The corrective signal is proportional to the difference between the potential Vset (related to the desired potential of the electrochemical system 150) and the detected potential Vmeas.

The cascaded amplifiers can control the potential of and/or current flowing into (or out) of the counter electrode 102. The output of the amplifier 120 (corrective feedback signal) can be electrically connected to the counter electrode 102 via impedance XM. The corrective feedback signal can, for example, set the potential of the counter electrode 102 to a desired potential (e.g., proportional to Vset), inject a corrective current into the electrochemical system 150, etc. A corrective current signal flowing into (or out) of the counter electrode can be detected by measuring a potential VTIA across the impedance XM (e.g., by a voltmeter) and dividing the measured potential VTIA by the impedance XM. As described before, by measuring the corrective current flowing into (or out) of the counter electrode for various input voltages Vset, a current versus voltage (I-V) graph can be generated. This I-V trace can contain the "fingerprint" of the analytes in the electrochemical system, and the identity of the analyte can be detected by comparing the detected I-V data with I-V data of other analytes.

An analyte (or multiple analytes) in an electrolyte can be detected by electrically coupling the electrochemical system (analyte and the electrolyte) to the potentiostatic apparatus 100 via the counter electrode 102, reference electrode 106 and working electrode 104. A user can set the voltage at the inverting input of the first amplifier 110 (e.g., by using a low noise tunable voltage source). The voltage buffer 160 can detect the voltage at the reference electrode without adding extrinsic noise and send a signal with a voltage value (related to the detected voltage) to the non-inverting input 110 of the first amplifier. Based on the two inputs the cascaded high-gain, low-noise negative feedback amplifiers (e.g., 110 and 120) send a corrective feedback signal (e.g., current signal) to the electrochemical system via the counter electrode. A feedback detection system in the potentiostatic apparatus 100 (e.g., a voltmeter, an ammeter, etc.) can detect the feedback signal. The feedback detection system can communicate with a control system (e.g., a computing device) that can record information related to the detected feedback. The control system can also control the value of the set voltage Vset. For example, the control system can sweep through series of values of the set voltage Vset, and record the corresponding feedback signal. The control system can generate a dataset of multiple set voltage values and the corresponding feedback signal (e.g., current). The control system can compare the generated dataset with datasets of feedback responses for other electrochemical systems (with different electrolytes, analytes, etc.), and determine the identity of the analyte in the electrochemical system at hand.

In other embodiments, the potentiostat can include two feedback loops (e.g., high-gain, low-noise feedback loops). The first feedback loop can control the potential at the reference electrode, and the second feedback loop can control the potential at the working electrode. The first and the second feedback loops can detect current flowing into (or out) of the working or counter electrode. The first and the second feedback loops can be independently controlled.

This exchange of energy at the working electrode can be mediated by the dielectric environment surrounding the donor and acceptor species (e.g., between redox species in the electrochemical solution 112 and the working electrode 104). The extent of involvement of the environment in the energy transfer process can depend on the nature of the electron transfer mechanism. In the case of adiabatic electron transfer, the electron transitions from the donor to the acceptor state (e.g., along an isoenergetic surface with a barrier) can be facilitated by, for example, temporal fluctuations in the intervening dielectric medium, such that the energy of the electron in the donor and acceptor states are comparable (e.g., equal at the time of transition). The dynamics of the transfer process can be determined by the accompanying relaxation of various nuclear vibrational modes (e.g., reaction coordinates) that follow the rapid oscillation of the electronic wavefunction between the donor and acceptor states. The rapid oscillation can occur, for example, due to the separation of the timescales between the dynamics of the transitioning electron and the slower, participant nuclear vibrational modes. On the other hand, non-adiabatic charge transfer can be characterized by the transition of the electron across multiple energy states. The electron transfer can involve exchange of several quanta of energy between the electron and the environment, for example, via a scattering process that can be accompanied by rapid environmental mode-relaxation. The bath vibrational modes involved in the dissipation of energy can be differentiated based on their differing frequencies. In the case of the adiabatic reaction a specific and limited number of modes designated together as a reaction coordinate vector can collectively map the evolution of the state of the system due to their direct participation in the limiting dynamics of the process. The electronic and nuclear time scales are non-separable in the non-adiabatic limit and the measured charge transfer rate can be representative of the convolved dynamics.

A microscopic theory that interpolates between the adiabatic and non-adiabatic charge transfer limits is presented, wherein polarity-based interactions and friction effects can influence the static reaction energetics and dynamics, respectively. A modification in the frictional coupling between the polarization modes of analytes (e.g., reaction coordinate modes) and the surrounding bath that slows or hastens the longitudinal relaxation of the participant solvent reaction coordinates and/or changes in the electronic coupling matrix element can be shown to induce the crossover between the two regimes, where the relaxation time for the coordinate modes is determined to be a function of the difference in dielectric polarization energy between the donor and acceptor states. The parameters that determine the nature of the interaction between the environment and the transitioning electronic wavefunction (e.g., the electronic coupling element, the relaxation time constant, and the like) can be treated independently. The parameters can be prescribed empirically, depending on the material properties of the solid and liquid phases of the electrochemical interface.

This application also prescribes two parameters characterizing the nature of the charge transfer reaction, that determine the strength of the electrostatic interaction between the tunneling electron and the reaction-coordinate, as well as between specific reaction-coordinate modes and their surrounding environment. The two variables can have an underlying and inverse dependence on the intrinsic charge at the interface separating the two species (metallic/semi-metallic electrode and redox active species) and are, in fact, not independent. Furthermore, the two parameters may be characterized as equivalent length scales that can be amenable to representation as equivalent circuit elements within a modified Randles circuit model of the interface. The characterization of the charge transfer process as current flow through a collection of model circuit elements can provide quantitative rules for the sizing of the interface based on the nature of the charge transfer mechanism.

A specific transfer mechanism—when the postulated length scales describing the electronic state-reaction coordinate interactions and the reaction coordinate-bath interactions are comparable to one another—can describe a resonant exchange of energy between the tunneling charge and a specific coordinate mode which can be of interest for the purpose of transducing vibrational mode information within the measured electron transfer rate. The electrochemical interface geometry can be described with the use of the parameters described above. An experimental prototype of the 'optimal' interface can be fabricated and characterized electrochemically to demonstrate the applicability of the proposed design rules.

Molecular model for electrolyte-specific redox species: An elementary 1D model for the vibronic structure of an electrolyte-dissolved molecular redox-active species is proposed here, from which two length scales are derived that describe the interactions between the electronic states of the redox active molecule and the harmonic states of the reaction coordinate, as well as the interactions between the bath and reaction coordinate degrees of freedom respectively. These length scales can be shown to characterize the nature of the charge transfer process based on the relative importance of the two interaction modalities they describe.

The potential energy of interaction between the electronic states of the redox active species and the surrounding electrostatic environment comprising of solvent polarization modes and other charged species is described by a conventional, continuum electrostatics formulation, in 1D, as described below:

$$V(x) = \frac{\left(-e\int dx''|\psi(x'')|^2\right)}{4\pi\varepsilon_o} \int dx' \frac{\rho(x')}{|x-x'|} + \frac{\left(-e\int dx''|\psi(x'')|^2\right)}{4\pi\varepsilon_o} \int dx' P(x') \cdot \nabla \frac{1}{|x-x'|} \quad (1.1)$$

where ρ and P are the free charge and reaction coordinate polarization densities associated with the surrounding electrostatic environment. The existence of the wavefunction terms in the R.H.S. of Equation (1.1) couples the potential energy to the solution of the Schrodinger's wave equation (SWE), requiring an iterative procedure for the estimation of the wavefunction. For a first order determination of the form of the solution, we set $\int dx''|\psi(x'')|=\alpha$, where $\alpha$ is an initial guess input to the iterative algorithm for the solution of the SWE and is a parameter between 0 and 1. The application of Gauss' law and boundary conditions at the metal-electrolyte interface yields a simplification of (1.1)

$$V(x) = \frac{-\alpha e}{4\pi x} Q_{int}\left(\frac{1}{\varepsilon_o} - \frac{1}{\varepsilon}\right) + \frac{(-\alpha e)}{4\pi\varepsilon}\left(\frac{Q_{int}}{x} + \sum_i \frac{q_i}{x-x_i}\right) \quad (1.2)$$

where $Q_{int}$ is the interface charge in the tunneling path between the metal and the redox active species dissolved in the electrolyte and $\Sigma q_i$, represents the collection of charges in the immediate environment of the redox species outside the transfer path of the tunneling charge. The first term on the R.H.S. represents the contribution to the potential energy of the electronic states from the coupling to neighboring reaction coordinate polarization densities and the second term represents the contribution from Coulombic coupling to the neighboring charges in the electrostatic environment around the redox molecule. In Equation (1.2), the interface is set at x=0. A solution for the SWE with the simplified potential energy function, as described in (1.2), described below, $$\left[\frac{-\hbar^2}{2m_e}\nabla^2 + V(x) + U_{N-N}([P_i])\right]\psi(x) = E\psi(x) \quad (1.3)$$

is obtained in a manner analogous to the problem of determining energy states of the hydrogen atom. $U_{N-N}([P_i])$ represents the self-energy of all the polarization states $P_i$ of the reaction system and this self-energy term varies on a significantly slower time-scale compared to V(x). The polarization and electronic degrees of freedom of the redox system are, thus, deemed separable under the Born-Oppenheimer approximation, and with this consideration, the energies of polarization-dressed electronic states are estimated as $$E_k = -\frac{m_e}{2k^2\hbar^2}\left(\frac{-\alpha e}{4\pi}Q_{int}\left(\frac{1}{\varepsilon_o}-\frac{1}{\varepsilon}\right) + \frac{(-\alpha e)}{4\pi\varepsilon}\left(Q_{int} + \sum_i q_i\right)\right)^2 + U_{N-N} \quad (1.4)$$

with $U_{N-N}$, defining the 'shifted' ground state for the redox system as a result of coupling with the polarization modes.

From a dimensional analysis of the expression of the electronic state energy in Equation (1.4), a length scale is proposed that describes the interaction between the electronic states of the redox moiety and its external electrostatic environment, which includes the polarization density harmonic oscillator states:

$$\lambda_{e-\Omega} = \frac{4\pi\varepsilon_o \hbar^2}{m_e e Q_{int}} \quad (2.1)$$

A large $\lambda_{e-\Omega}$ can correspond to a strong coupling between the reaction coordinates and electronic states, and would imply enhanced responsivity of the redox electronic states to perturbing potentials from sources external to the subsystem of electronic states. Another length scale that can characterize the self-energy of reaction coordinate modes that follows from the SWE description of the polarization-dressed redox electronic states is given by $$\lambda_{\Omega-n} = \frac{Q_{int}^2}{\hbar\Omega_m}\left(\frac{1}{n_{\Omega_m}^2 \varepsilon_o} - \frac{1}{\varepsilon_{\Omega_m}}\right) \quad (2.2)$$

where $\Omega_m$ is the largest mode frequency of the participant reaction coordinate modes. The parameter $\lambda_{\Omega-n}$ can represent the energy content of a collection of oscillatory degrees of freedom comprising of relevant reaction coordinates. A large $\lambda_{\Omega-n}$ can be indicative of increased energy transferred via dissipative forces to the coordinate modes during the charge transfer process. The largest mode frequency can be representative for the coordinate mode frequencies and can result in a conservative estimate for $\lambda_{\Omega-n}$.

Lumped equivalent circuit representations of charge transfer system: The interaction between electronic and reaction coordinate degrees of freedom as well as between the coordinate degrees of freedom of the reaction system can also be represented as equivalent capacitances by utilizing the phenomenological length scales described in the previous section. We define $$c_q = \frac{m_e e Q_{int}}{4\pi\hbar^2} \quad (3.1)$$

and $$c_n = \frac{\varepsilon_{\Omega_m}\hbar\Omega_m}{Q_{int}^2}\left(\frac{1}{n_{\Omega_m}^2\varepsilon_o} - \frac{1}{\varepsilon_{\Omega_m}}\right)^{-1} \quad (3.2)$$

as the 'quantum' and 'nuclear' capacitances per unit area. The quantum capacitance, as defined in Equation (3.1), is the electrochemical analog to the Luryi quantum capacitance for a two dimensional conductor and is a measure of the extent of screening of the redox electronic states by the reaction coordinate polarization modes. The nuclear capacitance is an estimate of the self-screening by the reaction coordinate polarization modes, and is a physical entity that is very similar to a classical capacitance but is specific to the field due to $Q_{int}$ alone. In addition, the interface geometry contributes to a distribution of charge that distinct from $Q_{int}$ and is either localized on surfaces that are not in the physical charge transfer path or manifests due to a classical field that is superposed on the transfer path.

Figure 2A:
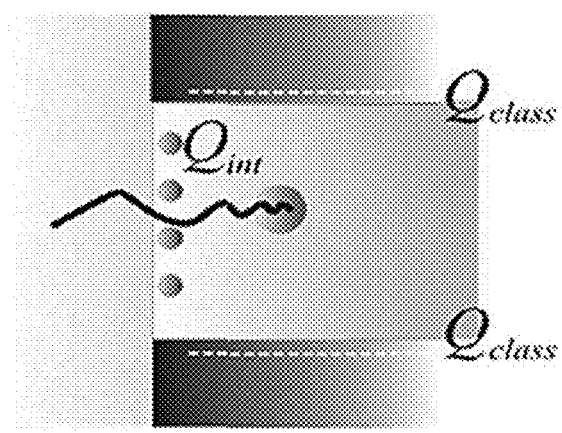
FIG. 2A illustrates an exemplary a charge transfer interface.
Figure 2B:
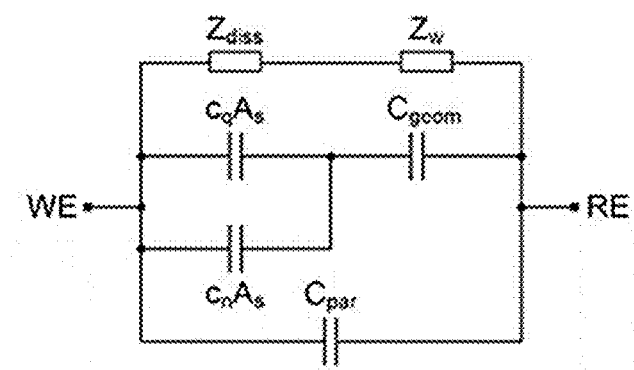
FIG. 2B illustrates a circuit representation of the charge transfer interface in FIG. 2A.

FIG. 2A illustrates a distribution of charge at an electrode-electrolyte interface (e.g., a working electrode of a potentiostat). Accordingly, the equivalent circuit representation for the charge transfer interface is depicted in FIG. 2B, where $C_{geom}$ and $C_{par}$ are classical capacitances arising from the geometry-dependent field in the charge transfer pathway and from the geometry of the interface exclusive of the tunneling path of charge transfer respectively. In addition, a non-linear dissipative element $Z_{diss}$ characterizes the bath coupled dynamics of a collection of harmonic reaction-coordinate oscillators, and a Warburg-type impedance element $Z_W$ can model the diffusional and field-driven electro-migration transport of reactants to the interface. For subsequent analysis, the transport-related limitations to the measured charge transfer rate can be ignored, and the transition dynamics accompanying the charge transfer process can be focused upon.

Figure 2C:
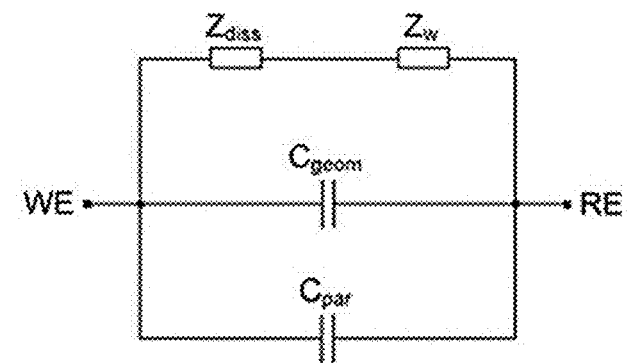
FIG. 2C illustrates the circuit representation of FIG. 2B in the limit $\hbar \rightarrow 0$.

The equivalent circuit description of the electrochemical interface in FIG. 2B reduces to the well-known, often-used Randles equivalent circuit in the classical limit that $\hbar"0$ (FIG. 2C). In a similar vein, the classical Randles circuit description can also be recovered for large and small $Q_{int}$, indicating that the magnitude of $Q_{int}$ can serve as a metric for the degree of quantum behavior at an electrochemical interface, like the Planck constant or temperature for other physical systems. The dependence of the nature of the system on interface charge can be non-monotonic (e.g., there can be an optimal magnitude of $Q_{int}$ for which the electrochemical interface manifests quantum behavior). In this context, a "quantum" electrochemical interface can be gated by $Q_{int}$ and can be characterized by interactions of comparable strength between the molecular electronic states and the harmonic polarization states associated with the reaction-coordinates, as well as between the reaction-coordinate polarization states themselves.

$$\lambda_{e-\Omega} = \lambda_{\Omega-n} \text{ or } c_q = c_n \quad (3.3a)$$

$$Q_{int}^{quant} \approx \left(\frac{4\pi\hbar^3 \varepsilon_{\Omega_m}\Omega_m}{m_e e\left(\frac{1}{n_{\Omega_m}^2\varepsilon_o} - \frac{1}{\varepsilon_{\Omega_m}}\right)}\right)^{1/3} \quad (3.3b)$$

Physically, Equations (3.3a,b) can imply a coherent exchange of energy between the electronic and polarization degrees of freedom upon the transition from the donor to acceptor configuration.

Figure 3A:
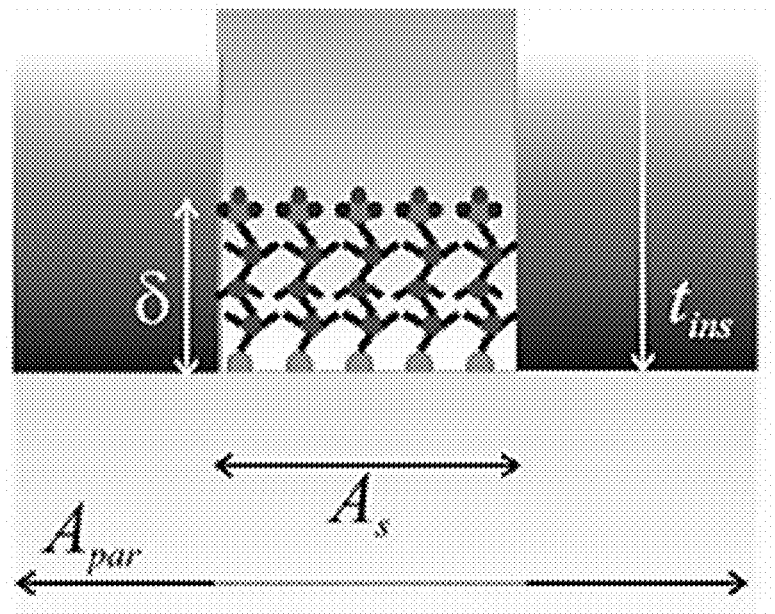
FIG. 3A illustrates an exemplary charge transfer interface for the nanoscale electrochemical sensor.

Geometric sizing rules for a quantum electrochemical interface: The representation of molecular interactions as lumped circuit elements can enables a quantitative estimation of the three dimensional geometry of the charge transfer interface. The interaction capacitances $c_q$ and $c_n$ can be compared with geometry-dependent capacitances that arise from the micro- and nanoscale structures at the electrochemical interface. This comparison can ensure that classical shielding effects arising from the electrostatic fields at these structures do not limit the interactions between the electronic and reaction-coordinate polarization states. The geometry of the interface comprises of an area $A_S$ where the electrode is coupled to the electrochemical solution (e.g., via a functionalization film), and across which active charge transfer occurs, and an insulating film of thickness $t_{ins}$ and dielectric permittivity $\varepsilon_{ms}$ that covers and insulates an area $A_{par}$ of the conductive metal surface. In addition, the area $A_S$ may be functionalized by a molecular film of thickness $\delta$ and permittivity $\varepsilon_m$ to impart specific electronic properties and/or surface chemistries to the charge transfer interface (FIG. 3A).

For the molecular thin-film, the requirement that quantum interaction effects, as described by $c_q$ or $c_n$ in the quantum limit (Equation 3.3), dominate over the classical screening of bath polarizations and charges across the thin film yields $$\frac{\delta}{\varepsilon_m} < \frac{4\pi\hbar^2}{m_e e Q_{int}^{quant}} \quad (4.1)$$

A similar consideration for the capacitance due the insulator between the electrolyte and the underlying metal electrode describes a lower limit for the ratio $A_S/A_{par}$ $$\frac{A_S}{A_{par}} > \frac{4\pi\hbar^2 \varepsilon_{ins}}{t_{ins} m_e e Q_{int}^{quant}} \quad (4.2)$$

The lateral dimensions for $A_S$ can be determined from an estimate of volume required to contain the equivalent thermal spread in the harmonic polarization density, when the spread is of sufficient magnitude ($\sim Q_{int}^{quant}$) to facilitate a transition event between the relevant polarization states solely via thermal excitation. The area $A_S$ can introduce a spatial limit on the reaction coordinate states that can sustain the polarization density variations necessary for thermalized charge transfer, which in turn stipulates an upper limit on the number of reaction modes that can contribute to the measured transition dynamics. For coherent polarization states, the uncertainty in the polarization state is given by $$\langle \Delta P_\Omega^2 \rangle = \left( \frac{\hbar \Omega}{2V_\Omega \left( \frac{1}{n_\Omega^2 \varepsilon_o} - \frac{1}{\varepsilon_\Omega} \right)} \right) (e^{-\gamma t} + (1 - e^{-\gamma t/2})^2) \quad (5.1)$$

where the time dependence in (5.1) occurs over the slower time-scales associated with the ensemble-averaged parameters like $\gamma$. The rationale for assuming coherence in the polarization presupposes a classical trajectory for the heavier nuclear modes under the influence of an external biasing field. $V_\Omega$ is the effective volume of the electrolyte ($A_S t_{ins}$ as defined by the geometry of the interface) that 'contains' the polarization mode in Equation (5.1). Therefore, the required lateral dimensions for gating the contributions from modes with frequencies smaller than $\Omega_m$ is given by $$A_S = \frac{(Q_{int}^{quant})^2}{\left( 1 - \frac{\varepsilon_o}{\varepsilon_{\Omega_m}} \right)^2} \left( \frac{2t_{ins}\left[ \frac{1}{n_{\Omega_m}^2 \varepsilon_o} - \frac{1}{\varepsilon_{\Omega_m}} \right]}{\hbar \Omega_m} \right) \quad (5.2)$$

Transition probabilities for contributions from coordinate modes with higher frequencies can tend to be thermalized for $A_S$ as estimated from (5.2).

The total energy for reorganization of the coordinate modes in the electronic transition can be determined from the equivalent electronic energy required or expended for transition from the donor to acceptor state for an interface in a static equilibrium nuclear configuration. In this context, the reaction reorganization energy as estimated from the previously-mentioned model of the redox system can be described by $$E_r \sim \frac{m_e}{2\hbar^2} \left( \frac{eQ_{int}^{quant}}{4\pi} \left[ \frac{1}{\varepsilon_o} - \frac{1}{\varepsilon} \right] \right)^2 \quad (6.1)$$

from Equation (1.4), where the contribution of the reaction-coordinate polarization to the potential energy of the redox electronic states is considered in the determination of the equivalent energy required for the electronic transition. The appropriate redox chemistry for the electrolyte phase can be selected using the criterion that reorganization energy, $\Delta_r$, of the redox couple can be close to but smaller than $E_r$ in magnitude. Such a rationale for selection can imply that with the chosen redox chemistry, a smaller magnitude of the interface charge exists in the tunneling path, i.e. $Q_{int}^{\Delta_r} < Q_{int}^{quant}$. The difference in the tunneling path charge from the optimum value is accounted for by the appropriate chemistry and thickness of the molecular thin film functionalizing the sensor interface. The tunneling barrier to overcome for the electronic transition to occur across the thin film depends on the coupling between the thin film and the donor ($h_{D-f}$), between the film and the acceptor species ($h_{f-A}$), as well as the coupling between the molecular units comprising the thin film ($h_{f-f}$) which are assumed to be equal.

The tunneling band an can be defied as $$\Delta E_{tunn} = \frac{\hbar^2}{8m_e} \left( \frac{2}{\zeta} Ln\left[ \frac{\Delta\varepsilon}{h_{f-f}} \right] + \frac{2}{\zeta_{f-A}} Ln\left[ \frac{\Delta\varepsilon}{h_{f-A}} \right] \right)^2 \quad (6.2)$$

In Equation (6.2), $\Delta\varepsilon$ is the tunneling energy gap, which is the energy required to liberate a hole from the acceptor species and locate it on the film valence band and $\zeta$, $\zeta_{f-A}$ are the thicknesses of the individual molecular units associated with thin film and the end-group functionalization chemistry that is in contact with the electrolyte respectively. The total charge transfer barrier, expressed non-dimensionally in units of thermal energy, for specific redox chemistry and for a particular functionalization and molecular film chemistry is $$\frac{E_r}{k_B T} = \frac{\Delta_r}{k_B T} + \beta_{f-f}\delta_{f-f} + \beta_{f-A}\delta_{f-A} \quad (6.3)$$

where $\beta_{f-f}$, $\beta_{f-A}$ are the electron hopping matrix elements of the film and the functional end group and $\delta_{f-f}$, $\delta_{f-A}$ are the thicknesses associated with the film and functionalization chemistry respectively. From (6.2), the electron hopping matrix elements are $$\beta_{f-f} = \frac{2}{\zeta_{f-f}} Ln\left[ \frac{\Delta\varepsilon}{h_{f-f}} \right] \text{ and} \quad (6.4a)$$

$$\beta_{f-A} = \frac{2}{\zeta_{f-A}} Ln\left[ \frac{\Delta\varepsilon}{h_{f-A}} \right], \quad (6.4b)$$

which are dependent on the geometry and the tunneling energy gap normalized by the respective coupling energies. Equations (5.2), and (6.1) in conjunction with (6.3) can define an architecture suited for an electrochemical interface operating in the quantum regime, subject to limitations prescribed by (4.1) and (4.2).

Figure 3B:
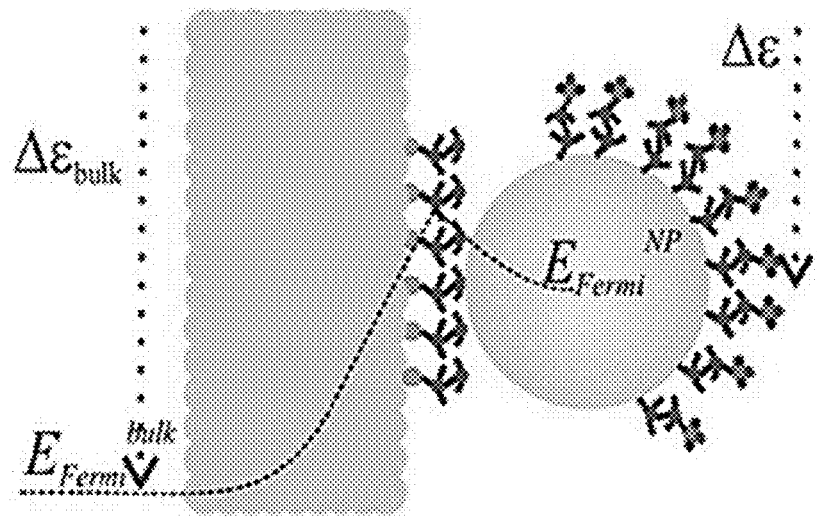
FIG. 3B illustrates an exemplary nanoparticle functionalization that can modulate tunneling energy barrier at a charge transfer interface.

Additional structures may be introduced at the interface for the reduction of the tunneling energy gap, which in turn can enable the use of thicker functionalization films. Thicker films are structurally more stable, available for functionalization off-shelf, with multiple functionalization chemistries and can be self-assembled onto the small sensing area $A_S$. These additional structures can also provide tolerances that guard against the formation of non-ideal films at the nanoscale interface. The functionalization of negatively charged, metallic nanoparticles onto $A_S$ with a molecular linker (FIG. 3B) can decouple the Fermi levels of the nanoparticle from the underlying macroscopic electrode. This can result in a built-in field at the interface that can reduce the effective tunneling energy gap associated with the rate-limiting tunneling path in the thicker film. The molecular linker used to tether the nanoparticle bridge can be thinner than the functionalization film thickness to ensure that the macroscopic electrode-linker-nanoparticle assembly does not become rate limiting in the tunneling path. Also, the nanoparticle can be larger than 2 nm in diameter for a Fermi level associated with a significant density of states to exist for the cluster of metal atoms. The reduced tunneling energy barrier can yield a thicker film that satisfies the energy balance in Equation (6.3) for the rate-limiting pathway. These thicker films, however, can be subjected to the equivalent thickness constraint outlined in Equation (4.1). The functionalization of the nanoparticle with the increased density of states at a higher energy may be thought of as equivalent to the existence of a surface state at the metal electrode surface with concomitant band bending of the Fermi energy at the interface. The distortion of the Fermi level at the interface can reduce the effective tunneling barrier for transport across the molecular film, resulting in a larger β value for the film. The incorporation of these additional degrees of freedom in the interface design allow for the use of a larger range of material chemistries in the fabrication of the electrochemical construct as well as allow for design tolerances to guard against non-ideal structures at the interface.

Figure 4C:
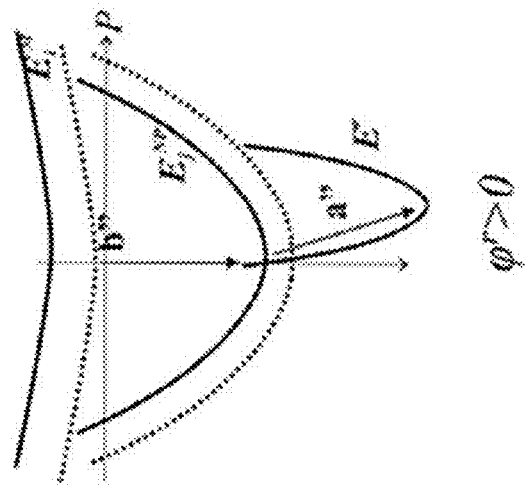
FIG. 4C illustrates an exemplary energy diagram depicting a charge transfer between a redox specie and an electrode when the bias between the redox state and the electrode Fermi level is sufficiently positive.
Figure 4B:
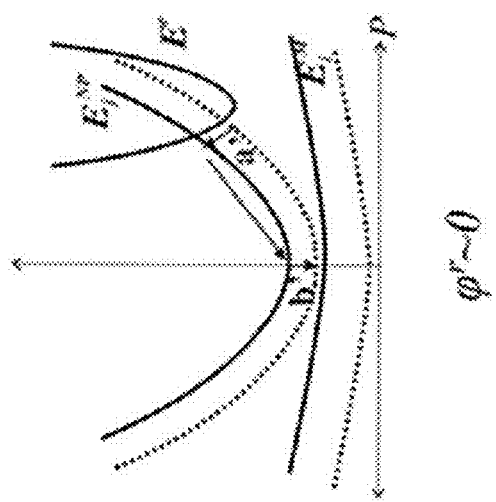
FIG. 4B illustrates an exemplary energy diagram depicting a charge transfer between a redox specie and an electrode when the bias between the redox state and the electrode Fermi level is near zero.
Figure 4A:
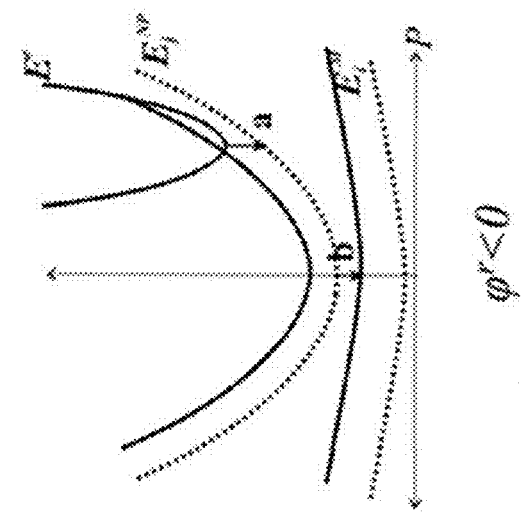
FIG. 4A illustrates an exemplary energy diagram depicting a charge transfer between a redox specie and an electrode when the bias between the redox state and the electrode Fermi level is sufficiently negative.

FIGS. 4A-C illustrate exemplary energy diagrams depicting charge transfer between a redox specie and electrodes with various fermi levels. The step changes in the transition current are associated with the opening of additional channels for electronic transition between donor and acceptor, wherein the access to the new channels is not constrained by an activation barrier and random thermal forces that can potentially disturb and dampen the barrier-free transitions are minimized. The open channel corresponds to the availability of resonant high energy reaction coordinate states that can exchange energy with the tunneling electron, facilitating the transfer event. The existence of multiple phonon states of the same modal frequency or the availability of new coordinate modes results in the opening of new channels that manifest as additional step-like features in the current voltage trace provided the mechanism for electronic transition via these new channels remains barrier-less.

The rate of transition of a charge from a donor to an acceptor when (i) $\lambda_\Omega(2n_{\bar{\Omega}}+1) \to 0$ for all $\Omega$ and (ii) when damping effects on the motion of the reaction coordinates are vanishingly small can be described by:

$$k_{d \to a} \propto \tag{6.5}$$

$$\sum_\Omega \lambda_\Omega^2 \gamma \Omega \left( 1 - \cfrac{1}{(\varepsilon_\Omega - \varepsilon_o)\left(\cfrac{1}{n_{\bar{\Omega}}^2 \varepsilon_o} - \cfrac{1}{\varepsilon_\Omega}\right)} \right)$$

$$\left( \left( \Delta \varepsilon - E_d + E_a - \sum_\Omega \Omega \left( 1 - \cfrac{1}{(\varepsilon_\Omega - \varepsilon_o)\left(\cfrac{1}{n_{\bar{\Omega}}^2 \varepsilon_o} - \cfrac{1}{\varepsilon_\Omega}\right)} \right) \right)^2 + \gamma^2 \right)$$

where $\Omega$ represents reaction coordinate mode, $\tilde{\Omega}$ and $\gamma$ represents a shift in the reaction coordinate mode and effective viscosity, respectively, due to interaction between the reaction coordinate mode and the bath, and $n_{\bar{\Omega}}$ represents the thermalized occupancy of the reaction coordinate oscillator energy levels. $\lambda_\Omega$ represents a non-dimensional measure of the shift between the harmonic potential energy surfaces of the reaction coordinate mode and is given by $$\lambda_\Omega = \frac{(P_a^\Omega - P_d^\Omega)V_\Omega}{(\hbar\Omega)^{1/2}} \left( \frac{1}{n_{\bar{\Omega}}^2 \varepsilon_o} - \frac{1}{\varepsilon_\Omega} \right)^{1/2} \tag{6.6}$$

where $P_i^\Omega$ is the polarization density of the harmonic reaction coordinate mode $\Omega$ in its ground state and associated with configuration i and $V_\Omega$ is the spatial volume required to sustain the modal oscillations.

Equation (6.5), when integrated over the band of available states in the underlying metal electrode, would yield the step-wise construct in the I-V trace of the nano-electrochemical interface that describes the availability of additional high frequency modes for enabling the transition. The width in the step-like features are determined from the magnitude of the damping kernel acting on the reaction coordinate polarization modes as a result of their interaction with the surrounding bath states. The utility of Equation (6.5) in describing the transition applies at low equivalent bath temperatures and for vanishing damping and reorganization energy barriers.

A conceptual description of the barrier-less transition, and its dependence on the applied bias is illustrated in the schematics of FIG. 4. The electronic energy states of the metal electrode and nanoparticle bridge constitute a band of available energies, defined as $E_i^M$ and $E_i^{NP}$ for i=1,2 etc., and $P_{bath}$ refers to the bath coordinate comprised of a linear combination of the distorting normal bath modes $P_k$. The redox molecule energy surface is also characterized by its electronic energy $E^r$, and the corresponding bath distortions around the ground electronic state. However, the bath distortions in the redox state are biased by relaxation of the dielectric polarization states as a result of dissipation of the reorganization energy upon charge transfer. Conceptually, the energy surfaces for the metal electrode, the nanoparticle linker and the redox molecule are given by $$E_i^M + \frac{k^M}{2}P_{bath}^2, \; E_j^{NP} + \frac{k^{NP}}{2}P_{bath}^2, \text{ and} \tag{6.6}$$

$$E^r + \frac{k^r}{2}\left(P - \alpha\sqrt{\Delta E_R}\right)^2$$

respectively, where $k^p$ is a measure of the coupling between the species p and its electronic state, $\Delta E_R$ is the reorganization energy for the charge transfer reaction and $\alpha$ is a dimensional constant. The schematics represent the energy surfaces for three different bias ranges, namely $\phi^r < 0$ (FIG. 4A), $\phi^r \sim 0$ (FIG. 4B) and $\phi^r > 0$ (FIG. 4C), where the bias $\phi^r$ is applied to the redox state via the reference electrode and is with respect to a grounded set of metal electronic states. The path to transition from redox state to metal electrode via the nanoparticle linker is without barrier for $\phi^r < 0$ as can be observed from FIG. 4A. Specifically, the manifold of available electronic states in the nanoparticle bridge allow for a direct transition from the redox ground state to a vibronic state on the nanoparticle element as indicated by the path a. Subsequently, a barrier-less charge transfer event occurs between the ground state of the nanoparticle linker and the underlying metal electrode (path b). The applied bias must be less than a threshold value for the first channel to open that enables the transfer from the ground redox state to the lowest vibronic nanoparticle state. For near resonance conditions between the metal Fermi level and the vibronic ground state of the redox molecule, the transition between the redox species and the nanoparticle bridge is thermally activated (path a' in FIG. 4B), and for off-resonance case, with φ'>0, the transition from the highest energy vibronic state of the nanoparticle element to the ground state of the redox moiety in the electrolyte (path "a" in FIG. 4C) is without barrier beyond a threshold positive bias voltage. Thus, the availability of the additional channels for transport occurs outside a bias window centered on the electronic resonance between the metal electrode and the redox active species, as also observed in FIGS. 7B and 7C.

A charge transfer interface can include an electrode (also referred to as "metallic micro-lead") that can be separated from the electrochemical solution by one or more of an insulator and a functionalization film. For example, the metallic micro-lead can be surrounded with one or more insulating layers on one or more exposed surfaces of the micro-lead. A portion of the insulating layer can be replaced with a functionalization film layer. An exchange of charge (e.g., a tunneling current) can occur between the metallic micro-lead and the electrochemical solution via the functionalization film layer.

In some aspects, metallic micro-lead can be coupled to a nanoparticle via a molecular linker layer. A portion of the insulating layer can be replaced by the molecular linker layer. The nanoparticle can be separated from the electrochemical solution via a functionalization film layer. An exchange of charge (e.g., a tunneling current) can occur between the metallic micro-lead and the electrochemical solution via the functionalization layer, the nanoparticle and the molecular linker layer.

Figure 5:
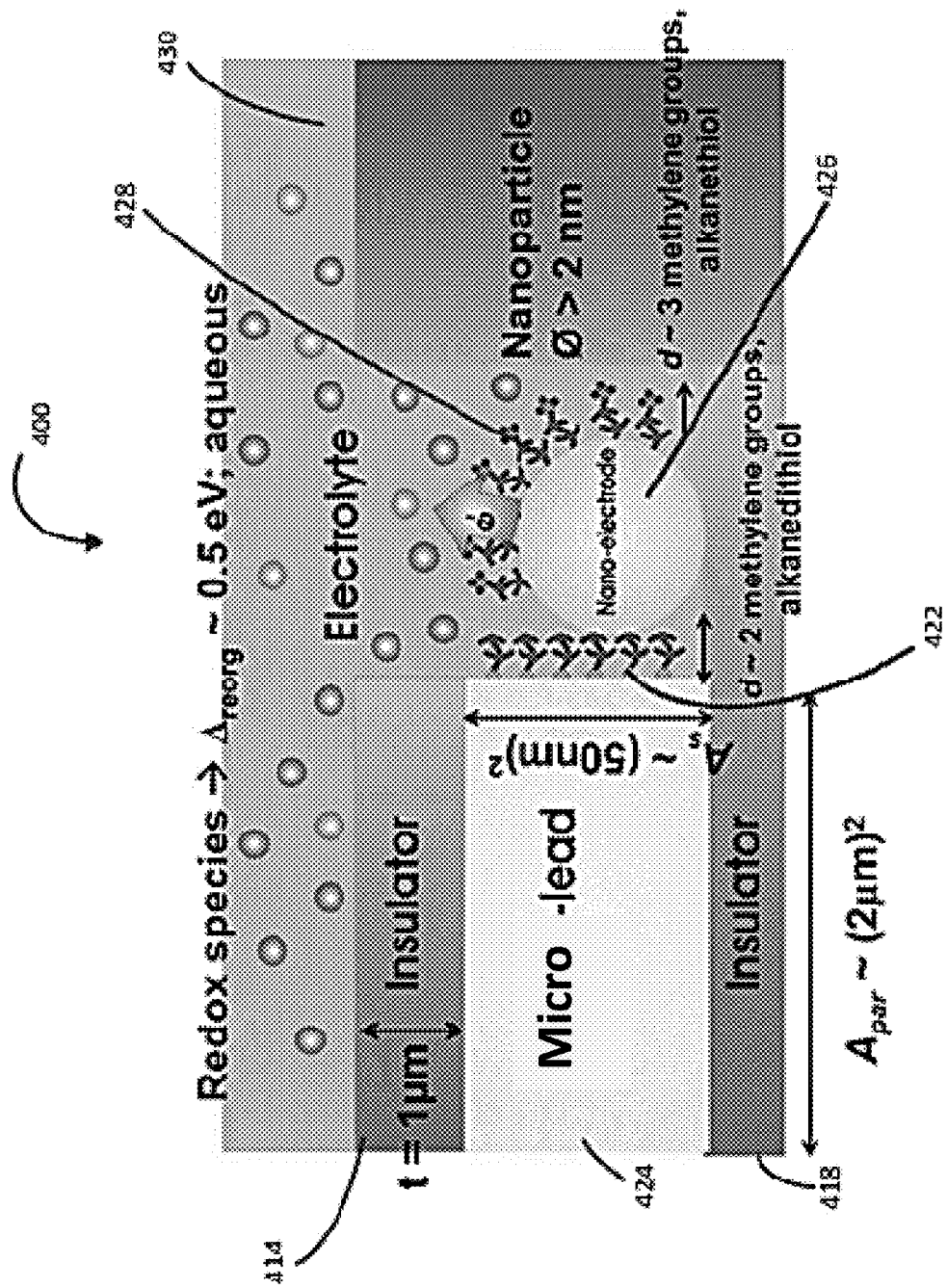
FIG. 5 illustrates an exemplary charge transfer interface with a nanoparticle functionalization.

FIG. 5 illustrates an exemplary charge transfer interface 400 with a nanoparticle functionalization. The interface 400 includes a metallic micro-lead 424 which can be coupled to insulator layers 414 and 418 via a top and a down surface, respectively. The micro-lead 424 can also be coupled to a molecular linker layer 422 via an exposed surface. The charge transfer interface 400 can also include a nanoparticle 426 which can be coupled to the micro-lead 424 via the molecular linker 422. The molecular linker layer 422 and the insulator 414 can prevent direct exchange of electrons between a redox species (e.g., redox species in an electrochemical solution 430) and the micro-lead 424. A functionalization layer 428 can separate the nanoparticle 426 and the electrochemical solution 430. A tunneling current can occur between the electrochemical solution 430 and the micro-lead 424 via the functionalization film 428, the nanoparticle 426 and the molecular linker 422.

An exemplary quantitative exposition of the interface geometry is outlined in FIG. 5 for (a) an organic alkanethiol monolayer as the functionalization thin film; (b) silicon dioxide (SiO$_2$) as the insulating film; (c) an aqueous electrolyte phase, comprising of a 100 mM phosphate buffer; (d) and cut-off maximum frequency $\Omega_m$ given by $1.5\times10^{14}$ rad/s respectively, given the design rules (4.2), (5.2) and (6.3), and transition rate for strong coupling limit. For the above choice of materials and mode frequencies characteristic of the interface, the upper limit of the functionalization film thickness δ is about $0.5\times10^{-9}$ m and the redox chemistry best suited for the interface is the ferro-/ferricyanide redox couple.

The length scales $\lambda_{e-\Omega}$ and $\lambda_{\Omega-n}$ described above can represent the interaction strength between the dressed electronic states of the redox species and the reaction coordinate modes as well as between the reaction coordinate modes themselves. The length scales can characterize the nature of the transport regime. A small $\lambda_{e-\Omega}$ and large $\lambda_{\Omega-n}$ can imply independent electronic and reaction coordinate degrees of freedom and dissipative charge transfer from donor to acceptor state, indicating an adiabatic transition event. A large and small $\lambda_{\Omega-n}$ interface can characterize an electronic transition with strong coupling to the nuclear modes, which can describe a non-adiabatic transition for $k_B T/\hbar\Omega_m \gg 1$. The inverse relationship between the two characteristic length scales follows from their respective dependencies on the tunneling path charge $Q_{int}$ as seen in Equations (2.1) and (2.2). The attenuation of the damping effects and of the thermalized disturbances acting on the charge transfer reaction at the quantum electrochemical interface as a result of the application of high gain feedback action can result in a smaller $\lambda_{\Omega-n}$ and a concomitantly larger $\lambda_{e-\Omega}$, which in turn arise from a smaller $Q_{int}$.

A mechanistic characterization of damping effects and thermal noise at the electrochemical interface and its relation to $Q_{int}$ is presented here that uses a Hamiltonian description of the energy of a single reaction coordinate mode, linearly coupled to a large collection of harmonic degrees of freedom, to estimate the dynamic evolution of the polarization density associated with the reaction coordinate mode. The reaction coordinate polarization mode can be subjected to bath-induced damping and random thermalized forces as a consequence of the linear coupling.

The Hamiltonian can be described as:

$$H_\Omega = \frac{1}{2}\left(\frac{1}{n_\Omega^2 \varepsilon_o} - \frac{1}{\varepsilon_\Omega}\right)\left[P_\Omega^2 + \frac{\dot{P}_\Omega^2}{\Omega^2}\right] + \sum_k \frac{1}{2}\left(\frac{1}{n_k^2 \varepsilon_o} - \frac{1}{\varepsilon_k}\right)\left(1 - \frac{\varepsilon_o}{\varepsilon_k}\right)^2\left[\sigma_k^2 + \frac{\dot{\sigma}_k^2}{\omega_k^2}\right] + \frac{P_\Omega}{\varepsilon_\Omega}\sigma_k \qquad (7.1)$$

where a unimodal, one dimensional reaction coordinate polarization density is assumed for the charge transfer system and bath degrees of freedom are multimodal though also one dimensional in nature. A linear coupling between the reaction-coordinate and bath modes can be considered in the evaluation of polarization dynamics. in the total tunneling path charge can be represented in terms of the modal tunneling path charge density $\sigma_k$ where $$\frac{Q_{int}(t)}{A_S} = \sum_k \sigma_k(t) \qquad (7.2a)$$

The reaction-coordinate polarization modes can be treated semi-classically for the sake of demonstrating the influence of feedback with a simpler, intuitive description and without loss of relevant physical facts. The equivalent damping coefficient and the amplitude of the thermal fields acting on the reaction coordinate polarization density are given by $$\gamma(t) = \frac{g(\Omega)\Omega^2}{\left(\frac{1}{n_\Omega^2\varepsilon_o} - \frac{1}{\varepsilon_\Omega}\right)\varepsilon_\Omega^2}\left[\sum_k \frac{\cos\omega_k t}{\left(\frac{1}{n_k^2\varepsilon_o} - \frac{1}{\varepsilon_k}\right)\left(1 - \frac{\varepsilon_o}{\varepsilon_k}\right)^2}\right] \qquad (7.3a)$$

$$E(t) = -\sum_k \frac{\sigma_{k_o}\cos\omega_k t + \frac{\dot{\sigma}_{k_o}}{\omega_k^2}\sin\omega_k t}{\varepsilon_\Omega} \qquad (7.3b)$$

respectively, where $\sigma_{k_o}$ and $\dot{\sigma}_{k_o}$ are the randomly determined values of tunneling path interface charge density and tunneling path charge flux respectively. The thermal fluctuation in bath field acting on the reaction coordinate polarization is directly related to fluctuations in the tunneling path interface charge as $$E(t) = -\frac{Q_{int}(t)}{A_S \varepsilon_\Omega} \quad (7.3c)$$

Accordingly, the power spectral density of the field fluctuations at the electrochemical interface is frequency independent, up to a cut-off frequency determined by the maximum frequency of the bath modes ($\omega_{k_{max}}$), with a magnitude that is determined by contributions from the individual mode components of the tunneling path charge density $$\langle \Delta E^2 \rangle = \frac{\sum_k \sigma_{k_o}^2 [\delta(\omega - \omega_k) + \delta(\omega + \omega_k)]}{2\varepsilon_\Omega^2 [1 + (\omega/\omega_{k_{max}})^2]} \sim \frac{1}{\varepsilon_\Omega^2 (1 + (\omega/\omega_{k_{max}})^2)} \int dk g(k) \sigma_o^2(k) \quad (7.4)$$

where the sum over all bath degrees of freedom in (7.3) is replaced by an integral of the contributions from the individual modal charge densities weighted by the density of states in the space of available modes. The fluctuations in the bath field, when referred to the input of the biasing feedback network, can describe the equivalent thermal noise source for the electrochemical system.

The measured fluctuation can be described as:

$$\langle \Delta E_{meas}^2 \rangle \approx \frac{\langle \Delta E^2 \rangle}{|1 + G(\omega)|^2} \quad (7.5)$$

where $G(\omega)$ is the frequency dependent closed loop gain of the feedback. Equation (7.5) presupposes an ideal noise-less feedback action applied on the physical interface by the accompanying electronics, which is modified by additional additive noise sources in the case there are added fluctuation sources from the feedback instrumentation. The gain also attenuates the damping forces acting on the reaction coordinate polarization density as $$\gamma_{eff}(\omega) \approx \frac{\gamma(\omega)}{\text{Re} G(\omega)} \quad (7.6a)$$

where $$\gamma(\omega) = \int dt e^{-j\omega t} \frac{g(\Omega)\Omega^2}{\left(\frac{1}{n_\Omega^2 \varepsilon_o} - \frac{1}{\varepsilon_\Omega}\right) \varepsilon_\Omega^2} \int dk g(k) \frac{\cos[\omega(k)t]}{\left(\frac{1}{n^2(k)\varepsilon_o} - \frac{1}{\varepsilon(k)}\right)\left(1 - \frac{\varepsilon_o}{\varepsilon(k)}\right)^2} \quad (7.6b)$$

The application of gain and the subsequent attenuation of the field fluctuations applied to the quantum electrochemical interface results in a reduction of $Q_{int}$ as seen from (7.3) and (7.5). The extent of the reduction is determined by the gain-bandwidth characteristic of the feedback system and the fluctuations imparted by the external signal chain to the physical system as seen from the input of the feedback loop, where a larger number of additional noise sources increase $Q_{int}$.

In addition, by the fluctuation-dissipation relationship, the effective bath temperature as 'seen' by the polarization mode associated with the reaction-coordinate is described by $$T_{eff} = \frac{\Omega^2}{\left(\frac{1}{n_\Omega^2 \varepsilon_o} - \frac{1}{\varepsilon_\Omega}\right) k_B} \frac{\langle \Delta E_{meas}^2 \rangle}{\gamma_{eff}} \quad (7.7)$$

in the semi-classical limit. The effective bath temperature can also be represented by T=1.13×10$^{48}$'($C_{int}$·PSD)$^2$ where PSD represents voltage noise power spectral density and $C_{int}$ is the interface capacitance. The interface capacitance should be dominated by quantum mechanical terms that depend on $Q_{int}$, namely $c_q$ and $c_n$. The bath temperature is attenuated by the closed loop feedback bandwidth and gain-dependent factor ReG($\omega$)/|1+G($\omega$)|$^2$ in the ideal case when the accompanying biasing network is noiseless. In the non-ideal situation, with contributions from noise sources in the instrumentation electronics, the bath temperature can be, accordingly, higher. The underlying dependence of the field fluctuations on $Q_{int}$ can make the tunneling path charge a surrogate for the effective bath temperature. In the scenario when there are multiple, independent and mutually normal coordinate polarization states participating in the transition process and not just a single mode as described above, $$\frac{Q_{int}(t)}{A_s} \sim \sum_k \sigma_k + \sum_\Omega \sigma_\Omega \quad (7.8)$$

The feedback affects the contribution to $Q_{int}$ (t) from the linearly coupled bath modes, k, that contribute to the thermal noise and the damping experienced by the transitioning system. Consequently, as the number of coordinate polarization states contributing to the observed transition rate increases, the feedback is less effective in modulating the dynamics of the transition, eventually culminating in the non-adiabatic charge transfer limit when the feedback action is likely to prove ineffective.

The description of the effect of high gain, low noise feedback action on a physical nano-electrochemical interface provided above assumes an interface operating in a quantum regime and not limited by classical phenomena, such as charge-transport through the interface geometric capacitance or transport-related effects. The attenuation of the damping forces and the thermal fluctuations acting on the reaction coordinate polarization dynamics are essential functions of the feedback system to retain the quantum nature of the interface, and the geometry of the interface may require adjustment as per the rules described previously to accommodate the influence of the electronics on $Q_{int}$.

Figure 6:
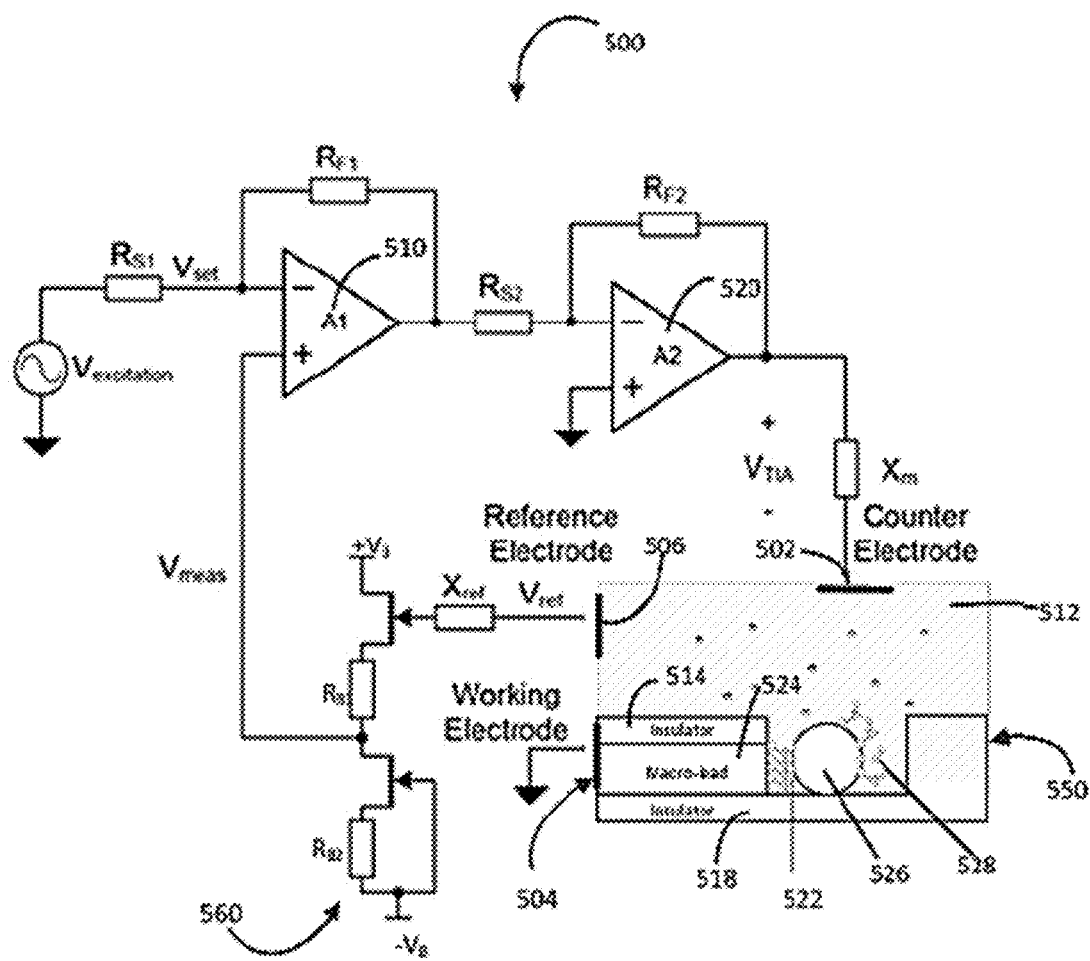
FIG. 6 illustrates an exemplary potentiostat having the charge transfer interface described in FIG. 5.

FIG. 6 illustrates an exemplary potentiostat 500 that includes the charge transfer interface 550 (e.g., charge transfer interface 400 described in FIG. 5). The potentiosat 500 described in FIG. 6 can be electrically coupled with an electrochemical system 512 via counter electrode 502, working electrode 504 and reference electrode 506. The potentiostat 500 can also include a high-gain, low noise feedback circuit comprising a buffer 560, and cascaded amplifiers 510 and 520. The potentiostat 500 and the electrochemical system 512 can interact, for example, as described in FIG. 1.

The working electrode 504 can include the charge transfer interface 550. The charge transfer interface 550 can include a metallic micro-lead 524 which can be coupled to layers of insulators 514 and 518 (e.g., via a top and a down surface, respectively). The micro-lead 524 can also be coupled to a molecular linker layer 522 via an exposed surface (e.g., a surface of the micro-lead 524 where a portion of the insulator layer 514 or 518 is replaced by a molecular linker layer). The charge transfer interface 550 can also include a nanoparticle 526 which can be coupled to the micro-lead 524 via a molecular linker layer 522. The molecular linker layer 522 and the insulator layers 514/518 can prevent direct exchange of electrons between the redox species in the electrochemical solution 512 and the micro-lead 524. A functionalization layer 528 can separate the nanoparticle 526 and the electrochemical solution 512.

A tunneling current can occur between the electrochemical solution 512 (e.g., one or more redox species in the electrochemical solution 512) and the micro-lead 524 via the functionalization film layer 528, the nanoparticle 526 and the molecular linker layer 522.

The properties of insulators 514 and 518, micro-lead 524, nanoparticle 526, functionalization film 528 and molecular linker layer 522 can be determined based on the electrochemical solution (e.g., redox species and analytes in the electrochemical solution, and the like). The properties can include geometry of the various components of the working electrode 504 (e.g., size, surface area, thickness, exposed area to the electrochemical solution, conductivity, dielectric constant, etc.).

EXAMPLE 1

A rapid prototyping approach has been considered for the fabrication of the sensor interface structure to enable a quick turn-around on the testing of the I-V characteristic of the interface for validation of the theoretical results presented in the previous section. A platinum (0.8)-iridium (0.2) wire (Nanoscience Instruments Inc., Alexandria, Va.) of 0.25 mm diameter is cut into smaller segments, 2 cm in length, and cleaned in standard SC-1 solution (100 ml DI water:10 ml $H_2O_2$:1 ml $NH_4OH$). The cleaned wire segment can then be mounted in a custom holder on a z-stage. The stage can lower the shorter wire segment into an electrochemical etch bath, comprising of 35 g sodium chloride (Sigma Aldrich, St. Louis, MO) and 2.9 ml of perchloric acid (Sigma Aldrich, St. Louis, MO) in 200 ml of DI water, in the middle of a ringed copper counter electrode also dipped in the etchant bath. An AC waveform with 60 Vpp amplitude at a frequency of 1 kHz can be applied between the wire segment and counter electrode, as the wire is dipped into the bath by lowering the z-stage. The end point of the etching process can be detected visually by cessation of the generation of hydrogen bubbles in the etchant bath and by the generation of a spark at the wire-tip at end point. The meniscus at the wire-etchant-air interface and the radial geometry of the etching setup results in a sharp tip-like profile at the breakpoint of the short wire segment. Upon completion of etching, the holder can be retracted and the etched wire segment can be retrieved for cleaning. The etched wire can be rinsed in DI water and dipped in SC-1 solution for a minute, prior to a repeat rinse with DI and subsequently blow dried with dry $N_2$.

A 40 nm-thick insulating oxide film can be deposited on the electrochemically etched wire using an atomic layer deposition (ALD) tool. Prior to deposition, the etched wires, if stored for more than 24 hours, can be sonicated carefully in ethanol and blow-dried with dry $N_2$. ALD can be specifically chosen as the deposition method of choice to ensure conformality of oxide on the etched surface of the tip wire and to avoid the formation of pinhole defects in the film that could result in an unwanted background of electrochemical leakage current in the measurement. The self-limiting nature of the ALD process can ensure monolayer-by-monolayer growth of the oxide film on the platinum iridium surface. For example, two types of insulating oxide films have been investigated experimentally: hafnium dioxide ($HfO_2$) and silicon dioxide ($SiO_2$). The Savannah thermal deposition tool (Ultratech Inc, Waltham, MA) and Fiji plasma deposition system (Ultratech, Waltham, MA) were used for depositing 40 nm of $HfO_2$ and $SiO_2$ respectively. Custom holders are used to mount the etched wires in the reactor chamber in a batch manner. A handle wafer is also simultaneously loaded into the reactor chamber, and the thickness of the deposited film is subsequently measured on the handle wafer with a M2000 Woollam Spectroscopic Ellipsometer. Prior to deposition of the primary oxide material, a 5 A seed layer of $Al_2O_3$ can be deposited on the platinum-iridium metal to ensure adhesion of the $HfO_2$ and $SiO_2$ precursors to the surface. After deposition of the oxide, the insulating film can be annealed in a furnace, in a forming gas (e.g., 20% $H_2$, 80% $N_2$ by volumetric flow rates) environment (e.g., at 300 C for 30 minutes) to remove any surface states on the oxide film that can contribute to parasitic charge transfer at the interface.

A hole of variable diameter can be subsequently milled in the annealed insulator film by a focused gallium ion beam on a Hitachi Dual Beam 235 SEM/FIB system. Custom holders are utilized to mount the annealed wires into the loadlock of the dual beam tool in batches of 10. The wire segments can be manually and sequentially aligned to the electron beam optics for imaging and the ion beam optics for milling. The ion-milled wire segments can be rinsed in ethanol and incubated in, for example, a) a 1 mM ethanolic solution of 1,2-ethanedithiol (Sigma Aldrich, St. Louis, MO) for 24 hours, b) an aqueous solution of gold nanoparticles (Sigma Aldrich, St. Louis, MO) of varying diameters for 24 hours and c) a 1 mM ethanolic solution of suitable alkanethiol monolayers (Sigma Aldrich, St. Louis, MO) with different functionalization chemistries for 48 hours. Post incubation, the tips can be rinsed with ethanol and blow dried with dry $N_2$ in preparation for loading into the electrochemical cell. The rinsed tips can be threaded through a pre-prepared Poly Di-Methyl Siloxane (PDMS) gasket, using a precision z-stage to manually pull the tips, blunt end first, through a hole in the gasket, while observing the height of the sharpened tip from the top surface of the gasket. The tip can be pulled through the gasket until the sharp tip protrudes 1 micrometer (um) or less from the upper surface of PDMS gasket. The gasket can be made, for example, by mixing 100:10 parts by volume of monomer and curing agent (Sylgard Dow Corning, Midland, MI), degassing the mixture in vacuum and curing at 50C. The gasket can be cut out of the cured block of PDMS material with dimensions 3cm×3cm×1 cm and the hole that houses the wire is cored in the middle of the gasket with a blunted syringe needle of 30 gauge inner diameter. The functionalized, ion-milled tip, once loaded in the PDMS gasket can be connected by a flexible wire connector to the alligator clip associated with the working electrode node on the potentiostat. The gasket with the embedded wire tip substrate is mounted on the bottom half of a Teflon electrochemical cell which can be secured to the top half by screws, with an O-ring forming a leak-proof, compression seal between the gasket and top half of the Teflon cell. The liquid electrolyte is an aqueous buffer comprising of a mix of potassium mono-and dihydrogen phosphate (Sigma Aldrich, St. Louis, MO) in DI water at a total concentration of 100 mM, in a ratio such that the solution is buffered at pH7.5. In addition, the aqueous electrolyte can contain a specific redox couple, decided upon by the nature of the experiment, at 1 mM concentration. Additional analyte species at requisite concentrations may be added to the electrolyte as per the requirements of the experiment at hand. 2.5 ml of the electrolyte solution can be pipetted into the well of the electrochemical cell. A gold wire (Alfa Aesar, Ward Hill, MA) and a Ag/AgCl reference electrode (BASi, West Lafayette, IN) can be secured to the alligator clips corresponding to the counter and reference electrode nodes respectively, and are each dipped in the electrochemical well to make contact with the electrolyte solution.

EXAMPLE 2

The current-voltage trace for a nano-electrochemical interface that is fabricated to specifications described above is acquired by application of a sweeping low-voltage noise bias between the interface and the Ag/AgCl reference electrode and the resulting current crossing the counter electrode-electrolyte interface is measured as a voltage drop across a series resistor at the counter electrode node by a low noise transimpedance amplifier chain. The custom low voltage noise potentiostat described in the previous section is utilized for the signal application and the current measurement. The bias is cycled between ±0.3V for the cyclic voltammetry experiment with a scan rate that is well below the maximum limit dictated by the characteristic time-scale for the integrated electrochemical interface-instrument system. For all the nanoscale electrochemical interfaces described in this paper, the limiting capacitance for the integrated system that determines the maximum scan rate is associated with the input capacitor of the buffer at the reference electrode node (~1 pF). The fastest allowable scan speed is ~1 mV/s, assuming sampling at each mV interval between the bias range of ±0.3V, and beyond the maximum scan rate the discharging of the buffer capacitance dominates the transient current measurement, obfuscating any signal associated with the donor-to-acceptor transition.

EXAMPLE 3

Figure 7A:
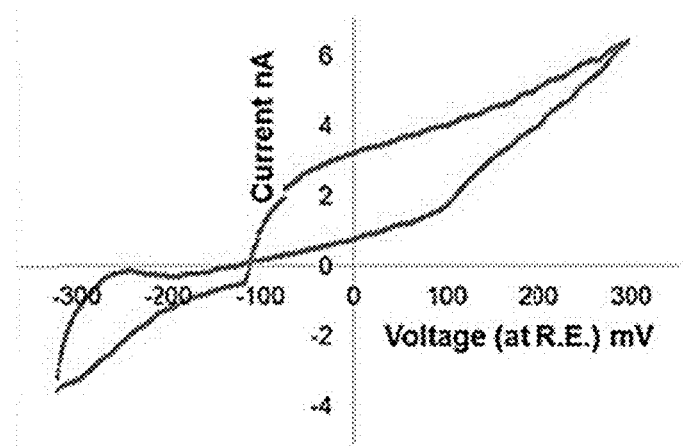
FIG. 7A illustrates an exemplary current-voltage characteristics for the charge transfer interface described in FIG. 5.
Figure 7B:
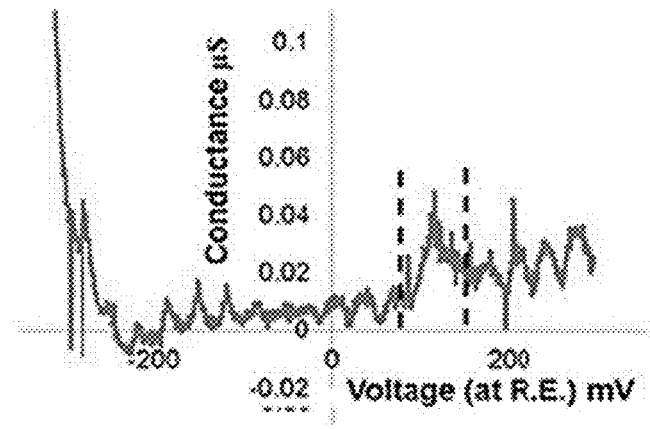
FIG. 7B illustrates an exemplary sampled conductance for a forward scan of the current-voltage characteristic in FIG. 7A.
Figure 7C:
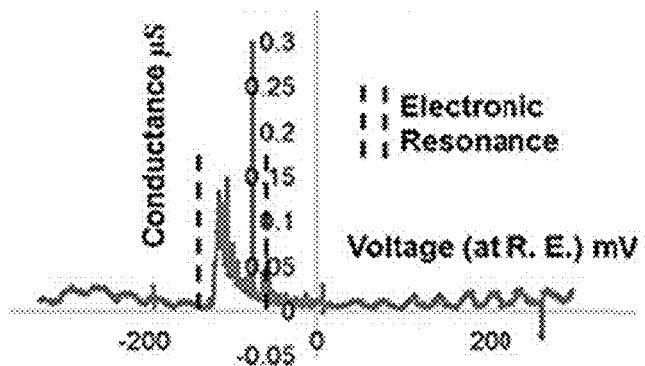
FIG. 7C illustrates an exemplary sampled conductance for a reverse scan of the current-voltage characteristic in FIG. 7A.
Figure 7D:
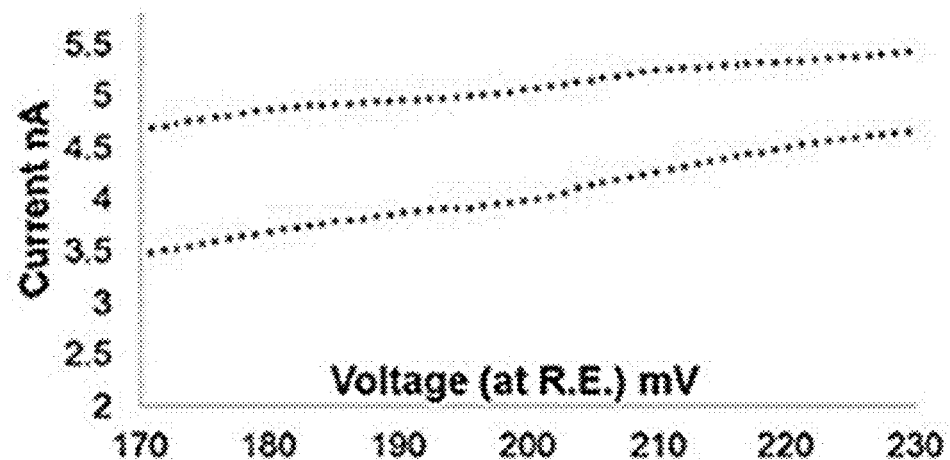
FIG. 7D illustrates an exemplary segments of the current-voltage trace in FIG. 7A corresponding to 60 minutes of data acquisition.
Figure 7E:
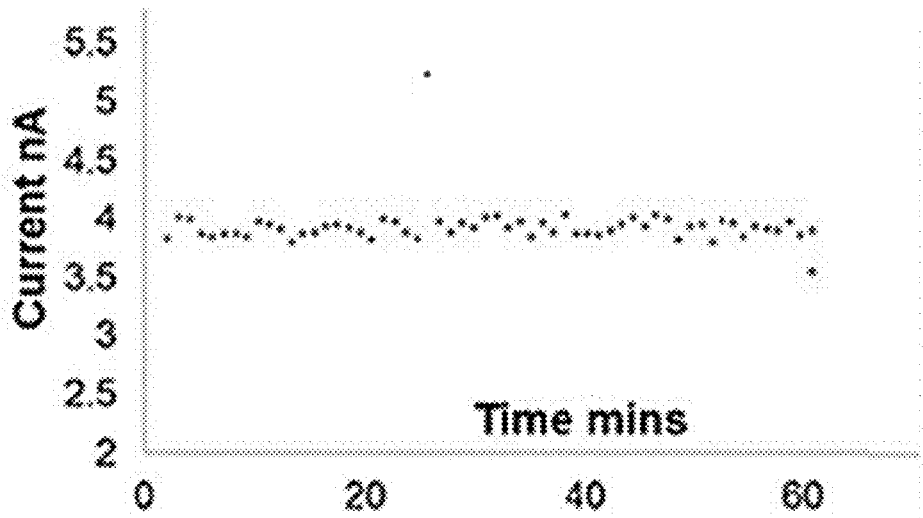
FIG. 7E illustrates an exemplary chronoamperometry measurement for DC bias of 200 mV for a time period of 60 minutes.
Figure 8A:
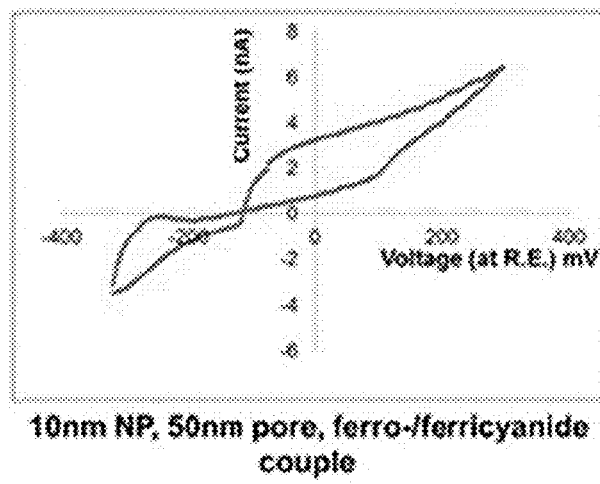
FIGS. 8A, 8B, 8C and 8D illustrate an exemplary current-voltage traces for various nanoparticle size, pore size and reorganization energy.
Figure 8B:
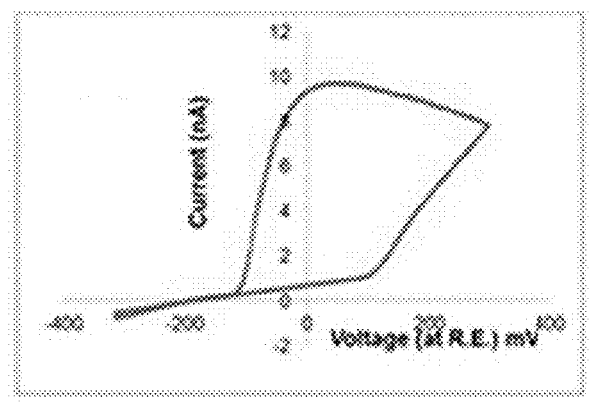
Figure 8C:
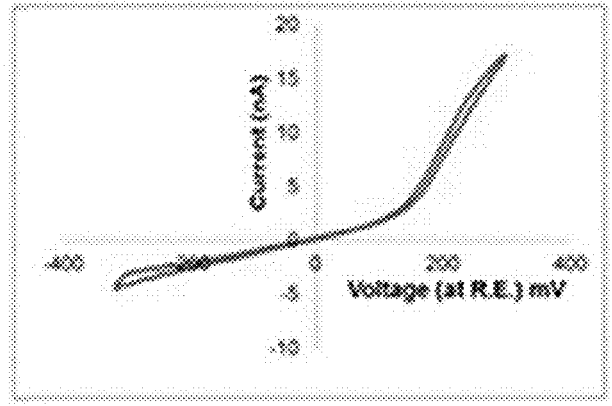
Figure 8D:
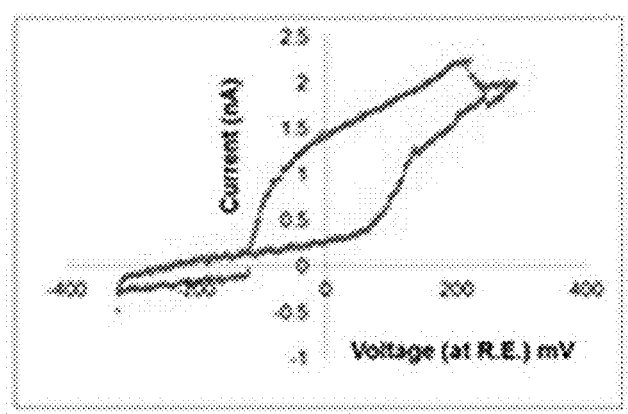

A typical I-V characteristic for the quantum electrochemical interface is demonstrated in FIG. 7A, for a 50 nm interface area, functionalized by a monolayer-nanoparticle-monolayer sandwich that comprises of sequentially self-assembled 1,2-ethanedithiol, 10 nm gold nanoparticles and 1-mercapto-3-propanoic acid on the exposed 80-20 platinum-iridium substrate. The electrolyte comprises of 100 mM potassium mono- and dihydrogen-phosphate in a ratio that sets the pH of the electrolyte at 7.5. The electrolyte also contains the potassium hexacyano (II and III) ferrate redox couple at 1 mM concentration. The arrows depict the acquired current traces for the forward (−0.3V to 0.3V) and reverse (0.3V to −0.3V) scans, with a scan rate of 1 mV/minute. The current, measured on every 1 mV voltage increment, is an average of a thousand acquired data points sampled over a 30 second interval, with a 30 second delay instituted prior to the acquisition for transient effects to dissipate sufficiently before the measurement. The I-V in FIG. 7A demonstrates a non-classical hysteresis between the forward and reverse scan traces that persists at the slow scan speeds, with well defined 'turn-on' and 'turn-off' bias points for the measured current. The hysteresis seen here is ascribed to the presence of $Q_{int}$, the interface charge in the path of the electronic tunneling transition, which biases the energies of the participant molecular redox states between the forward and reverse scans, analogous to the polaronic mode of electronic transport. The presence of countable quanta of electronic charge due to the charge transfer event at the nanoscale electrochemical interface influences the coupling of the electronic states to the nuclear polarization densities and induces a shift in the electronic energy of the electrolyte participant state, which is most strongly coupled to the interface charge, by an amount proportional to the energy required to charge the interface to $Q_{int}$. Thus, the hysteresis is utilized to estimate the equivalent interface capacitance for a quantum electrochemical interface engineered to the specifications outlined before, where the magnitude of $Q_{int}$ is calculated from Equation (3.3b). The equivalent interface capacitance, as determined from the measured hysteresis, serves as a sanity check to ensure that the geometric and classical capacitive impedances at the interface are not dominating over the quantum characteristics determined by $c_q$ and $c_n$. The equivalent capacitance thus calculated also provides a rough estimate of a parameter that can otherwise not be measured experimentally within the constraints of the custom built instrument comprising of off-the-shelf components. Table 1 lists the values of the different components of the total interfacial capacitance as calculated from Equations (3.1-3.3), and the calculated interfacial capacitance from the measured hysteresis. The near-convergence of the theoretical and estimated values for the quantum interface capacitance indicates that the classical capacitance is not limiting in the charging of the interface. The existence of step-like increases in the transition current is also observed in FIG. 7A for different ranges of applied bias. These quasi-discrete changes in measured current are observed clearly in the graphs for differential conductance versus applied voltage for the forward (FIG. 7B) and reverse (FIG. 7C) scans, where they manifest as collections of peaks in specific bias ranges. A chronoamperometric measurement, wherein the averaged transition current was acquired over a period of 60 minutes at a voltage bias of 200 mV, enabled a comparison between the variations in the measured current with time (FIG. 7E) against the magnitude of the quasi-discrete increase in current in the I-V characteristic (FIG. 7D) to ascertain that the observed discrete features are not arising from transport-specific oscillations in the reaction flux at the interface with time.

EXAMPLE 4

The nature of the hysteresis and the appearance of the barrier-free channels in the I-V traces can be modulated by modifying the geometry and the redox chemistry at the nano-electrochemical interface, as seen in FIGS. 8A-D. For all traces demonstrated in FIGS. 8A-D, the underlying metal electrode is platinum (80%)-iridium (20%), the metal to gold nanoparticle linker is 1,2-ethanedithiol and the monolayer on the nanoparticle ("NP") is 1-mercapto-3-propionic acid. The gold nanoparticle is 10 nm in diameter (FIG. 8A) and the redox chemistry used is the ferro-ferri-cyanide couple, unless indicated otherwise. The default insulator coating on the etched tip is 40 nm thick hafnium oxide and the milled hole is 50 nm wide. Reducing the nanoparticle size to 5 nm (FIGS. 8B-D) yields a current-voltage characteristic with larger hysteresis, with more pronounced turn-on and turn-off voltages and without the presence of the vibronic conduction channels. The functionalization of the interface with smaller nanoparticles increases the effective charge transfer flux area and simultaneously also reduces the effective tunneling energy gap $\Delta\varepsilon$ due to increased Fermi level distortion at the metal-1,2 ethanedithiol interface. The reduced tunneling energy gap results in higher transition currents and compensates for the increased $Q_{int}$ due to increased area. Increasing the interface area to 1 μm×1 μm and reducing the nanoparticle size to 5 nm yields a further increase in $Q_{int}$, resulting in smaller overall transition rates and less pronounced electronic resonance features. The large interface area results in increased thermal contributions from high frequency modes as described above, yielding a reduced transition rate as well, wherein barrier-less resonant transfer channels are not available for charge transfer. The use of hexaamine ruthenium (II and III) chloride as the interface redox couple instead of the ferro-/ferri-cyanide redox chemistry results in a complete collapse of the hysteresis (FIG. 8C) and the appearance of a classical I-V characteristic for the electrochemical interface. The ruthenium-based redox chemistry has a reorganization energy that is nearly twice as large as the reorganization energy for the ferro-/ferri-cyanide couple. Consequently, $c_q$ for the ruthenium chemistry is large enough that the system is limited by the classical components of the impedance, rendering the charge transfer process largely non-adiabatic in nature.

EXAMPLE 5

Figure 9A:
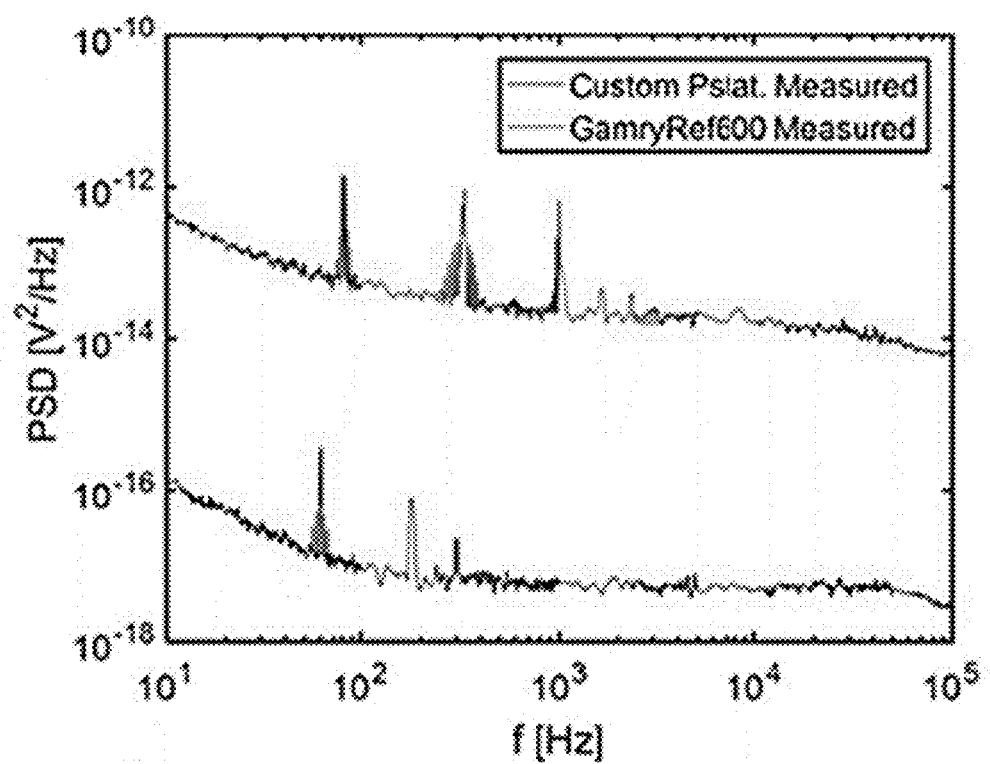
FIG. 9A illustrates an exemplary effect of high-gain and low-noise feedback circuit on the power spectral density (PSD) of voltage noise.
Figure 9B:
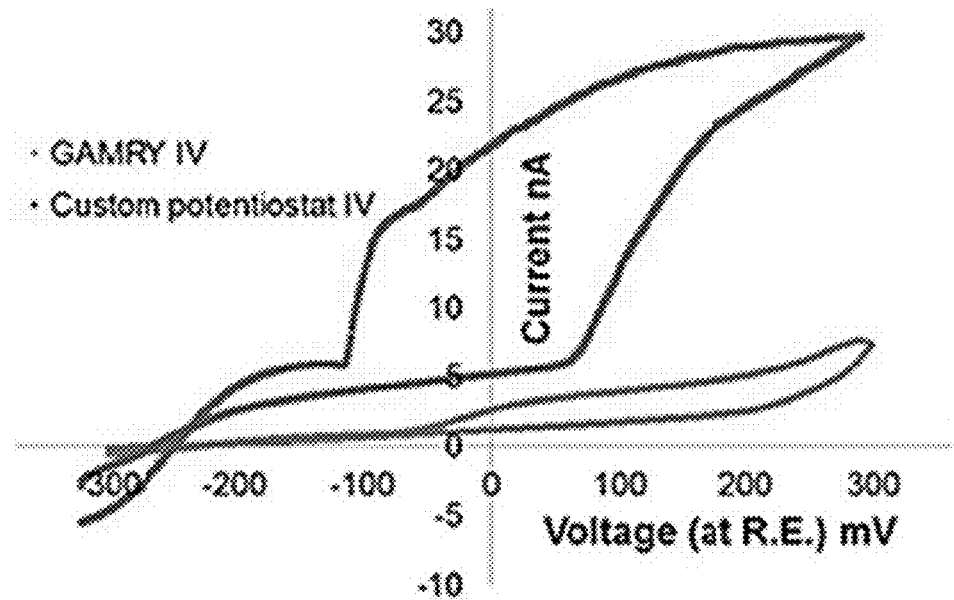
FIG. 9B illustrates an exemplary current-voltage trace for 40 nanometer thick $SiO_2$ insulating film, with and without low voltage noise PSD.
Figure 9C:
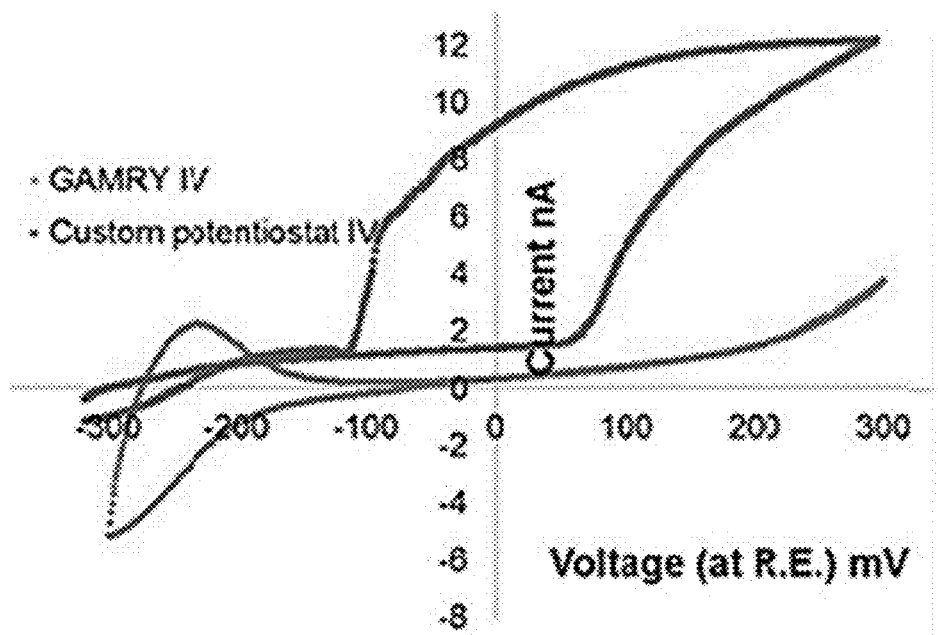
FIG. 9C illustrates an exemplary current-voltage trace for 40 nanometer thick $HfO_2$ insulating film, with and without low voltage noise PSD.

The effect of the low-voltage noise signal application at the interface as well as the application of the high-gain feedback for attenuation of damping effects in charge transfer, at the nanoscale interface, is demonstrated in FIG. 9 by contrasting the measurements made on the same interface type by two different potentiostats—the first instrument being our custom, low noise board and the second, a commercially available, off-shelf instrument of GAMRY-make. The nanoscale interfaces considered here comprise of a 50 nm ion milled pore in a 40 nm insulator film that coats electrochemically-etched platinum (80%)-iridium (20%) tip. The interface is functionalized by a heterogeneous self-assembled film comprising of 1,2-ethanedithiol, a 5 nm gold nanoparticle and 1 propanethiol, unless otherwise indicated. The equivalent voltage noise at the reference electrode node, referenced to the input of the feedback loop, is measured by a low noise amplifier for the GAMRY Ref 600 potentiostat as well as for our instrument as shown in FIG. 9A, which demonstrates the superior noise performance of the custom board. Increased voltage noise at the reference node results in quasi-classical I-V traces for nano-electrochemical interfaces that are subject to biasing by the feedback network on the GAMRY instrument, wherein electronic resonances and the hysteresis due to discrete charging effects are both suppressed, and the I-V trace, particularly in the case of the hafnia-coated interface (FIG. 9C), is classically adiabatic in nature as would be expected for a high $Q_{int}$ interface with no damping attenuation. The difference in the I-V characteristic between the silicon dioxide and the hafnium dioxide interfaces in FIGS. 8B and 8C, specifically when the GAMRY is used for the cyclic voltammetry measurement, suggests that the geometric capacitance from the coating oxide determines if the interface charge transfer is in the quantum or classical regime, as expected from the model proposed earlier. For the smaller parasitic capacitance arising from the silicon dioxide insulator, the charge transfer process appears to have quantum characteristics in the resonance features and the presence of the hysteresis, which are absent in the IV-trace for the hafnia-coated insulator. The differences between I-V characteristics of the two oxides persist when the interfaces are subject to the low voltage noise, high gain feedback, indicating that the oxide material chemistry continues to play an important role in determining classical, parasitic contributions independent of the feedback action, wherein the hafnia dielectric coated interface exhibits lower overall current and more diffuse turn-on and turn-off transitions.

EXAMPLE 6

Figure 10A:
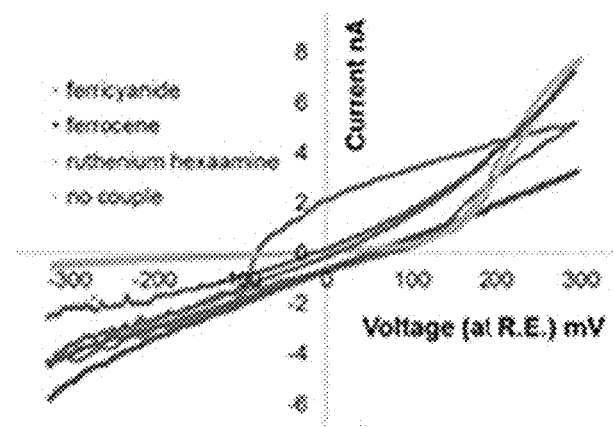
FIG. 10A illustrates current-voltage trace where an electrolyte is 100 mM of potassium mono- and dihydrogen phosphate and the metallic substrate is Pt (80%)-Ir (20%) etched into a sharp tip.
Figure 10B:
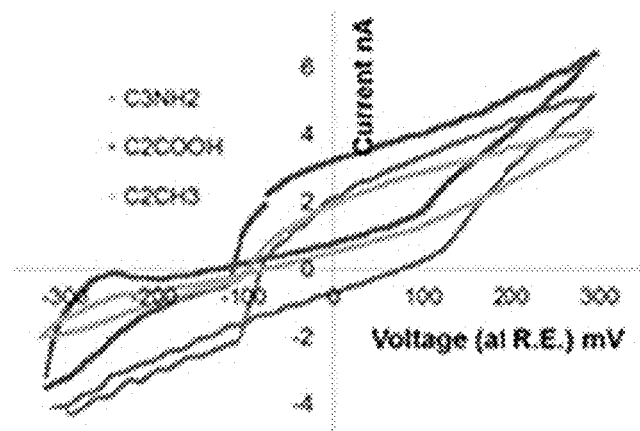
FIGS. 10B and 10C describe the current-voltage and conductance-voltage traces for interface comprising of 50 nm milled hole in a hafnia coated insulator, functionalized by monolayer assembly comprising of 1,2-ethanedithiol, 10 nm gold nanoparticles and a three carbon alkanethiol monolayer with variable end group chemistry, and the redox species used is the ferro-/ferricyanide couple.
Figure 10C:
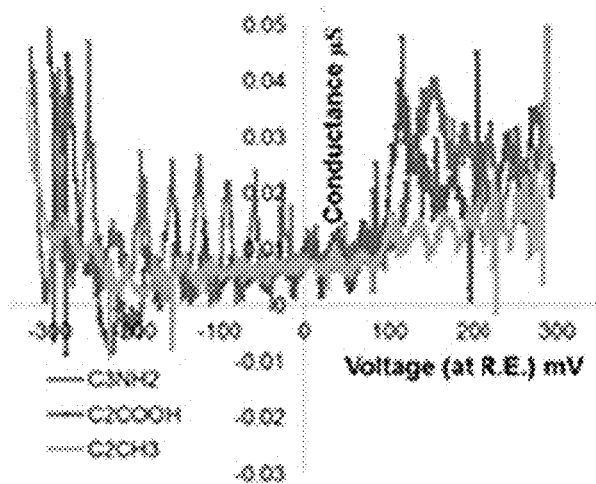
Figure 10D:
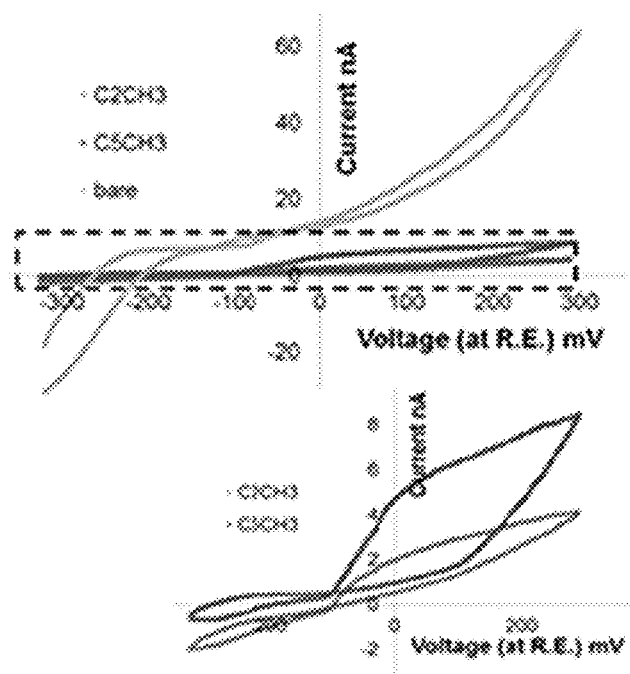
FIGS. 10D and 10E describe the current-voltage and conductance-voltage traces for interface comprising 50 nm hole in 40 nm thick hafnia dielectric, where underlying metal is functionalized by 1,2-ethanedithiol, 10 nm nanoparticles and films of differing thickness (inset in FIG. 10D illustrates a close-up of I-V traces for 1-hexanethiol and 1-propanethiol) and the redox species used is the ferro-/ferricyanide couple.
Figure 10E:
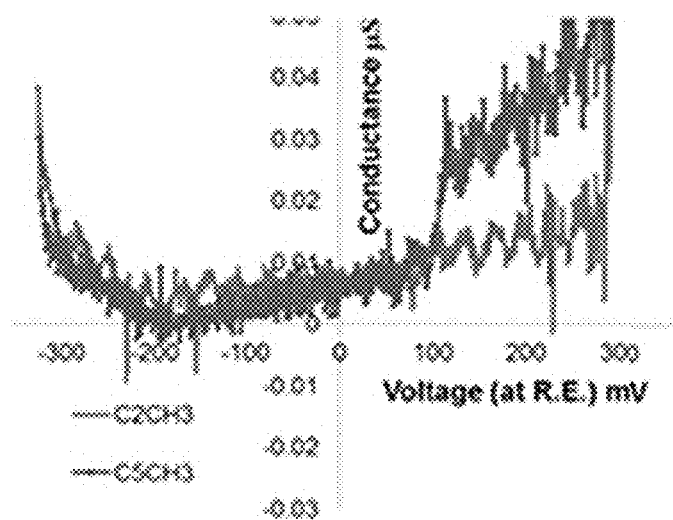
Figure 10F:
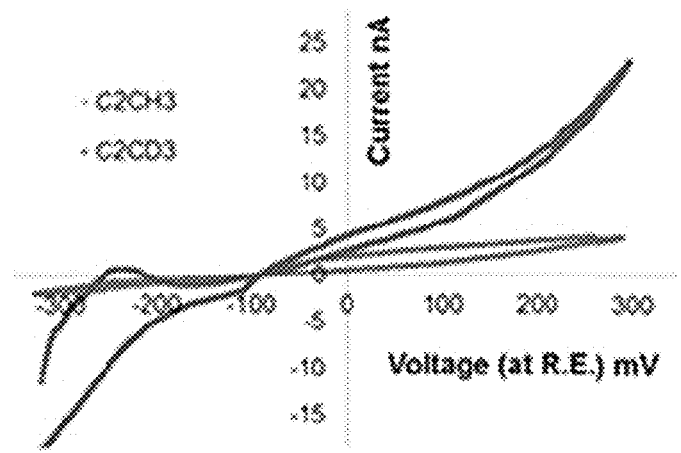
FIGS. 10F and 10G describe the current-voltage and conductance-voltage traces for interface comprising 50 nm hole in 40 nm thick hafnia dielectric, where underlying metal is functionalized by 1,2-ethanedithiol, 10 nm nanoparticles and deuterated and hydrogenated alkanethiol monolayer films that are three carbon atoms thick, and redox species used is ferro-/ferricyanide couple.
Figure 10G:
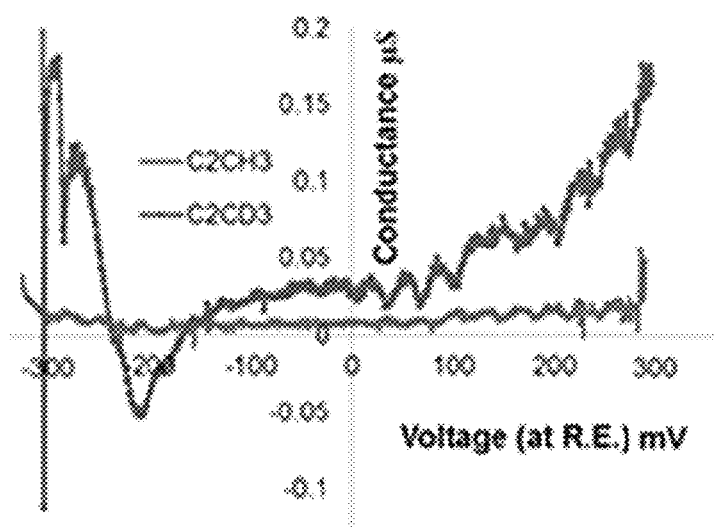

FIG. 10A illustrates the effect of redox chemistry on the transfer kinetics. The redox couples $Fe[CN]_6^{3-,4-}$, $Ru[NH_3]_6^{2+,3+}$, the ferrocene redox system and a redox-free electrolyte were considered for these measurements, wherein the interface is a 50 nm milled node in a hafnia coated insulator that was functionalized by a monolayer assembly comprising of 1,2-ethanedithiol, 10 nm gold nanoparticles and 3-amino-1-propanethiol. The electrolyte-dissolved redox moieties display I-V behaviors ranging from the purely quantized/discretized to the purely classical, in increasing order of reorganization energy associated with the charge transfer system ($Fe[CN]_6^{3-,4-}$<ferrocene<$Ru[NH_3]_6^{2+,3+}$<Redox-free electrolyte). FIGS. 9B and 9C demonstrate the effect of terminal end chemistry at the functionalization monolayer on the nanoparticle. The redox chemistry consistently used in this set of experiments was the $Fe[CN]_6^{3-,4-}$ couple and the monolayer end-chemistry was rotated between —NH$_2$, —COOH and —CH$_3$. The interaction between the charge on the end group and the negatively charged redox entity influences the tunneling energy gap, which, in turn, determines the $Q_{int}$ value as seen from Equation (6.4) and the efficiency of the tunneling transition in transducing information about vibrational channels available for the charge transfer process. FIG. 10C graphs the forward scan conductances for the different monolayer end-groups, depicting the improved resolution in the discrete channel signatures in the order —CH$_3$—COOH<—NH$_2$. The effect of functionalization monolayer thickness is demonstrated in FIGS. 9D and 9E. The interface comprises of a 50 nm milled pore in a 40 nm thick hafnia film, and the underlying metal is functionalized by the 1,2-ethanedithiol, 10 nm gold nanoparticle heterogeneous film. The nanoparticle is then subsequently either kept bare, or functionalized by 1-propanethiol or by 1-hexanethiol to generate the I-V traces recorded in FIG. 10D. The bare nanoparticle interface is characterized by a near classical I-V graph, whereas the monolayer-functionalized-nanoparticle interfaces are characterized by the discrete/quantized charge I-Vs with well-defined hysteresis and turn-on/-off voltages as seen in the inset. The conductance from the forward scan (FIG. 10E) indicates a decreasing resolution in the transduction of vibrational channels for the thicker functionalization film, since a thicker film would result in increased interactions between the larger numbers of reaction polarization modes present in the tunneling path and the redox vibronic states. The increased number of mode channels presented to the tunneling electron at a given bias results in loss of resonance between the polarization modes and the electronic states, rendering the polarization modes indistinct from the bath degrees of freedom. However, the discreteness of the electronic resonances is more pronounced and the magnitude of the measured current is also higher for the thicker monolayer. A thicker film between the nanoparticle electrode and the electrolyte-dissolved redox active species uncouples the electronic degrees of freedom between the donor and acceptor states qualitatively rendering the transition more non-adiabatic in nature. Consequently, $Q_{int}$ for a thicker film is lower than that for a thinner film, subject to the film thickness being below the threshold value prescribed by (4.1), and in the quantum regime, a lower $Q_{int}$ would yield larger transition rates and reduced damping associated with transition dynamics as seen in Equations (6.1) and (7.3) respectively. Qualitatively, the increased numbers of vibrational channels available for the transition result in larger transfer rates, as long as classical fields due to the interface geometry do not become rate-limiting. Mass-effects on the charge transfer reaction in the quantum regime are explored in FIGS. 9F, 9G. In these experiments, as in the previous measurements, the interface is a 50 nm milled pore in a 40 nm thick hafnia insulator that is functionalized by the 1,2-ethanedithiol linker and the 10 nm gold nanoparticle. The functionalization monolayer on the nanoparticle is varied between 1-propanethiol and 1-propane-d7-thiol where all hydrogen atoms are replaced by the heavier isotope deuterium. A reduced reaction polarization mode frequency, due to substitution by the heavier isotope, results in a smaller $Q_{int}^{quant}$ as seen from Equation (3.3b). Therefore, with the existing choice of redox chemistry (ferro-/ferri-cyanide couple), functionalization monolayer thickness and chemistry, the actual $Q_{int}$ value is likely to be larger in magnitude than the optimum $Q_{int}^{quant}$, making the transfer process, qualitatively, more adiabatic in nature. The resulting I-V trace for the non-optimal interface has reduced hysteresis and less pronounced turn-on and turn-off transitions at the electronic resonances as seen in FIG. 10F. However, the forward scan conductance (FIG. 10G) continues to exhibit the presence of resonant vibrational channels that participate in the transition process.

EXAMPLE 7

Figure 11A:
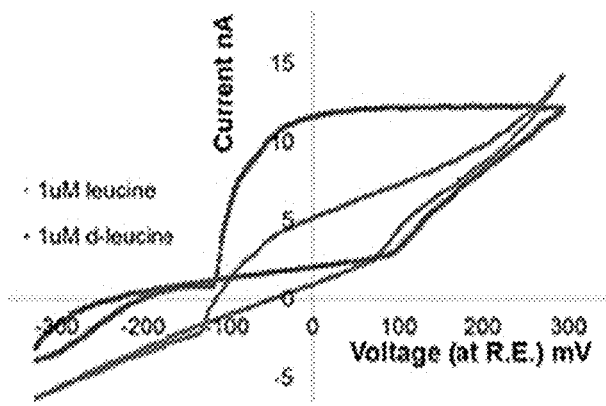
FIG. 11A illustrates a current-voltage graph for an interface.
Figure 11B:
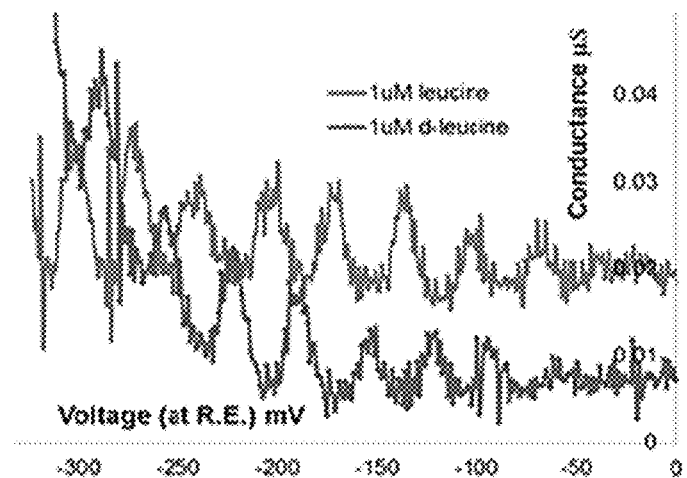
FIG. 11B illustrates a segment of the conductance trace corresponding to the current-voltage graph in FIGS. 11A and 11C.
Figure 11C:
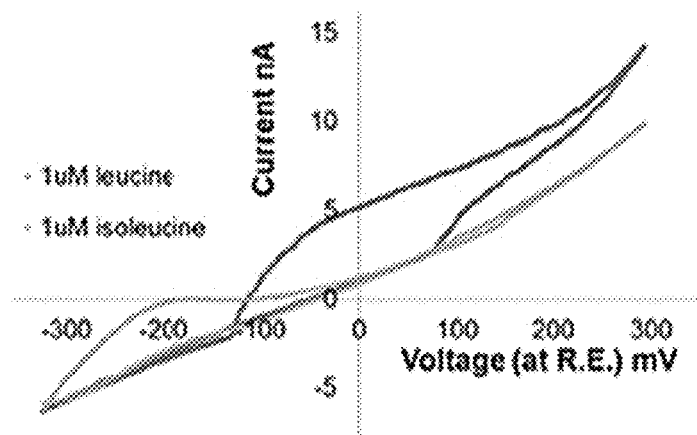
FIG. 11C illustrates a current-voltage graph for the interface in FIG. 11A.

FIG. 11 illustrates the sensitivity of the nano-electrochemical interface to electrolyte-dissolved analytes. In each example, the sensor (e.g., nano working electrode of a potentiostat) is a 50 nm ion-milled pore in 40 nm thick hafnium oxide insulator that coats an electrochemically etched platinum (80%)-iridium (20%) wire and the exposed metal is functionalized by a heterogeneous film comprising of 1,2-ethanedithiol as a linker, a 10 nm gold nanoparticle and 1-mercapto-3-propionic acid. The redox chemistry used in each instance is the ferro-/ferri-cyanide couple at 1 mM concentration, where the background electrolyte is a phosphate buffer at 100 mM concentration as with all previous experiments. The analyte, itself, is dissolved at 1 µM concentration for each experiment described here, and is varied between the isotope and isomers of the amino acid leucine. FIG. 11A compares the I-V traces for the nanoscale electrochemical interfaces, for the case when the electrolyte-dissolved analyte species is leucine or 2-d-leucine, where the hydrogen atom on the carbon adjacent to the carboxyl group of the leucine molecule is substituted by deuterium. FIG. 11C compares the I-V characteristics for the case when the dissolved analyte is leucine versus its structural isomer, isoleucine. The I-V trace for the deuterated analyte exhibits a larger hysteresis as seen in FIG. 11A, whereas isoleucine has a quasi-classical response to a low voltage noise scanning bias as observed in FIG. 11C. The diversity in response of the nano-electrochemical interface to the mass as well as structure of the analyte suggests sensitivity of the transition flux, as measured from the electrochemical charge transfer current, to intrinsic vibrational modes of the analyte and the presentation of these modes to monolayer functionalization chemistry. Though a mechanistic description of the precise manner in which the analyte orients at the end group chemistry by virtue the hydrogen bonds and the van der Waals interactions is beyond the scope of this manuscript, the presence of the analyte at the end group-electrolyte interface puts it in the direct tunneling path of the electron and therefore, analyte polarization states can potentially contribute additional channels for the transition event to occur. FIG. 11B contrasts the conductance data for the cases when the analyte is 1 µM leucine versus 1 µM 2-leucine and the vibrational channels for the 2-d-leucine analyte are all seen to have shifted to lower bias values by 20 mV on average with a standard deviation of 3 mV. The nearly uniform shift in the channel energy to a reduced bias is consistent with the reduced mode frequency associated with the deuterated analyte.

What is claimed is:

1. A sensor configured to detect an analyte, the sensor comprising:
    a metal electrode having a surface;
    an insulator film having a first thickness, a first surface area and a first surface chemistry, the insulator film coupled to the metal electrode via a first portion of the surface; and
    a functionalization film having a second thickness, a second surface area and a second surface chemistry, the functionalization film coupled to the metal electrode via a second portion of the surface,
        wherein a portion of the insulator film is replaced by the functionalization film and the first thickness of the insulator film and the second surface area of the functionalization film define a well configured to surround and contain an electrochemical solution over the metal electrode.

2. The sensor as in claim 1, wherein the insulator film and the entire second surface area of the functionalization film are configured to contact the electrochemical solution.

3. The sensor as in claim 1, wherein the insulator film has a first dielectric constant and the functionalization film has a second dielectric constant different from the first dielectric constant.

4. The sensor as in claim 3, wherein one or more of the first surface area, the first thickness, the first dielectric constant and the first surface chemistry are determined based on a threshold characteristic capacitance associated with the metal electrode and the electrochemical solution.

5. The sensor as in claim 3, wherein one or more of the second surface area, the second thickness, the second dielectric constant and the second surface chemistry are determined based on a characteristic charge distribution at an interface between the sensor and the electrochemical solution, wherein the interface is configured to transfer current between the sensor and the electrochemical solution, the transferred current indicative of the analyte in the electrochemical solution.

6. The sensor as in claim 1, wherein the electrochemical solution comprises one or more redox active species.

7. The sensor as in claim 6, wherein the one or more redox species are selected based on characteristic reorganization energies of the one or more redox species.

8. The sensor as in claim 7, wherein a transfer of charge occurs between the redox active species and the metal electrode via a portion of the functionalization film, wherein the metal electrode is biased relative to the electrochemical solution.

9. The sensor as in claim 1, wherein the insulator film includes a shielding mechanism configured to shield the metal electrode from a parasitic capacitance associated with the electrochemical solution.

10. The sensor as in claim 1, wherein the second surface area is determined based on a characteristic frequency of one or more polarization modes of a redox specie in the electrochemical solution, wherein the redox specie is configured to transfer charge to the metal electrode via the functionalization film.

11. The sensor as in claim 1, further comprising a feedback mechanism configured to detect a potential associated with the electrochemical solution via a first electrode and provide a feedback signal to the electrochemical solution via a second electrode.

12. A system comprising:
- a first electrode configured to electrically couple to an electrochemical solution;
- a second electrode configured to electrically couple to the electrochemical solution; and
- a third electrode comprising a sensor configured to detect an analyte in the electrochemical solution, the sensor comprising:
  - a metal electrode having a surface;
  - an insulator film having a first thickness, a first surface area and a first surface chemistry, the insulator film coupled to the metal electrode via a first portion of the surface; and
  - a functionalization film having a second thickness, a second surface area and a second surface chemistry, the functionalization film coupled to the metal electrode via a second portion of the surface,
  - wherein a portion of the insulator film is replaced by the functionalization film and the first thickness of the insulator film and the second surface area of the functionalization film define a well configured to surround and contain the electrochemical solution over the metal electrode.

13. A method of analyte detection comprising:
- detecting, by a feedback mechanism via a first electrode of a plurality of electrodes, a potential associated with an electrochemical solution, wherein the plurality of electrodes electrically coupled to the electrochemical solution;
- generating, by the feedback mechanism, a feedback signal; and
- providing the feedback signal to the electrochemical solution via a second electrode of the plurality of electrodes, the feedback signal configured to provide excitation control of the electrochemical solution at a third electrode of the plurality of electrodes,
  - wherein the third electrode includes a sensor configured to detect an analyte in the electrochemical solution, the sensor comprising:
    - a metal electrode having a surface;
    - an insulator film having a first thickness, a first surface area and a first surface chemistry, the insulator film coupled to the metal electrode via a first portion of the surface; and
    - a functionalization film having a second thickness, a second surface area and a second surface chemistry, the functionalization film coupled to the metal electrode via a second portion of the surface,
    - wherein a portion of the insulator film is replaced by the functionalization film and the first thickness of the insulator film and the second surface area of the functionalization film define a well configured to surround and contain the electrochemical solution over the metal electrode.

14. The method of claim 13, further comprising contacting the electrochemical solution with the insulator film and the entire second surface area of the functionalization film.

15. The method of claim 13, wherein the insulator film has a first dielectric constant and the functionalization film has a second dielectric constant different from the first dielectric constant.

16. The method of claim 15, further comprising determining one or more of the first surface area, the first thickness, the first dielectric constant and the first surface chemistry based on a threshold characteristic capacitance associated with the metal electrode and the electrochemical solution.

17. The method of claim 15, further comprising:
- determining one or more of the second surface area, the second thickness, the second dielectric constant and the second surface chemistry based on a characteristic charge distribution at an interface between the sensor and the electrochemical solution; and
- transferring current between the sensor and the electrochemical solution via the interface, the transferred current indicative of the analyte in the electrochemical solution.

18. The method of claim 13, wherein the electrochemical solution comprises one or more redox active species.

19. The method of claim 18, further comprising selecting the one or more redox species based on characteristic reorganization energies of the one or more redox species.

20. The method of claim 19, further comprising voltage biasing the metal electrode relative to the electrochemical solution, wherein a transfer of charge occurs between the redox active species and the metal electrode via a portion of the functionalization film due to the voltage bias.

* * * * *